United States Patent
Lendvay et al.

(10) Patent No.: US 10,147,052 B1
(45) Date of Patent: Dec. 4, 2018

(54) AUTOMATED ASSESSMENT OF OPERATOR PERFORMANCE

(71) Applicant: C-SATS, Inc., Seattle, WA (US)

(72) Inventors: Thomas Sean Lendvay, Seattle, WA (US); Adam Muir Monsen, Seattle, WA (US); Derek Alan Streat, Seattle, WA (US); Navdeep S. Dhillon, Seattle, WA (US)

(73) Assignee: C-SATS, Inc., Seattle, WA (US)

( * ) Notice: Subject to any disclaimer, the term of this patent is extended or adjusted under 35 U.S.C. 154(b) by 0 days.

(21) Appl. No.: 15/882,938

(22) Filed: Jan. 29, 2018

(51) Int. Cl.
| | |
|---|---|
| *G06F 15/18* | (2006.01) |
| *G06N 99/00* | (2010.01) |
| *G06Q 10/06* | (2012.01) |
| *G06N 5/02* | (2006.01) |

(52) U.S. Cl.
CPC ........... *G06N 99/005* (2013.01); *G06N 5/022* (2013.01); *G06Q 10/0639* (2013.01)

(58) Field of Classification Search
CPC ..................................................... A61B 34/30
USPC ............................................. 706/12, 15, 45
See application file for complete search history.

(56) References Cited

U.S. PATENT DOCUMENTS

| | | | |
|---|---|---|---|
| 2008/0007572 A1 | 1/2008 | Lewis et al. | |
| 2011/0179385 A1 | 7/2011 | Li et al. | |
| 2013/0209980 A1* | 8/2013 | Kuchenbecker | G09B 23/285 434/262 |
| 2014/0099082 A1 | 4/2014 | Miller | |
| 2014/0373033 A1 | 12/2014 | Chen | |
| 2015/0044654 A1* | 2/2015 | Lendvay | G09B 23/28 434/262 |
| 2015/0074033 A1 | 3/2015 | Shah | |
| 2015/0088884 A1 | 3/2015 | Shah | |
| 2015/0161903 A1 | 6/2015 | Colliander | |
| 2015/0269857 A1 | 9/2015 | Feng | |

(Continued)

FOREIGN PATENT DOCUMENTS

KR 1020090041160 A 4/2009

OTHER PUBLICATIONS

International Search Report and Written Opinion for International Application No. PCT/US2016/067758 dated May 11, 2017, 10 pages.

(Continued)

*Primary Examiner* — David R Vincent
(74) *Attorney, Agent, or Firm* — John W. Branch; Lowe Graham Jones PLLC

(57) ABSTRACT

Embodiments are directed to assessing performances of physical activities. Assessment engines may collect performance content that includes information associated with performances of activities. The assessment engines may employ classifiers to classify the performance content to determine occurrences of features of the performance content and classify assessment content to determine scores that are associated with features included in the performances. The assessment engines may provide correlation values associated with the performances based on historical performance content, assessment content, or scores. The assessment engine may provide a report that includes a localized evaluation of the performances based on the correlation values, performance content, assessment content, and scores. In some cases, the performance content may include videos of the performances.

28 Claims, 16 Drawing Sheets

(56) References Cited

U.S. PATENT DOCUMENTS

| | | | |
|---|---|---|---|
| 2015/0339940 A1* | 11/2015 | Aggarwal | G09B 7/02 |
| | | | 704/235 |
| 2016/0073227 A1* | 3/2016 | Han | H04W 4/02 |
| | | | 455/457 |
| 2016/0335778 A1 | 11/2016 | Smits | |
| 2017/0116873 A1* | 4/2017 | Lendvay | G09B 5/02 |

OTHER PUBLICATIONS

Pakhomov, D. et al., "Deep Residual Learning for Instrument Segmentation in Robotic Surgery", Mar. 24, 2017, 9 pages.
Official Communication for U.S. Appl. No. 14/922,867 dated Dec. 27, 2017, 3 pages.
Official Communication for U.S. Appl. No. 14/922,867 dated Oct. 10, 2017, 21 pages.
Official Communication for U.S. Appl. No. 14/922,867 dated Mar. 13, 2017, 20 pages.
Official Communication for U.S. Appl. No. 14/922,867 dated Jul. 28, 2016, 5 pages.
Official Communication for U.S. Appl. No. 14/922,867 dated May 17, 2016, 23 pages.
Official Communication for U.S. Appl. No. 14/922,867 dated Feb. 3, 2016, 14 pages.

\* cited by examiner

FIG. 4   REVIEWERS 420

| | 1 | 2 | 3 | 4 | 5 |
|---|---|---|---|---|---|
| Depth Perception | Constantly overshoots target, wide swings, slow to correct | Some overshooting or missing of target, but quick to correct | | | Accurately directs instruments in correct plane to target |
| Bimanual Dexterity | Uses only one hand, ignores non-dominant hand, poor coordination | | Uses both hands, but does not optimize interactions between hands | | Expertly uses both hands in a complementary way to provide best exposure |
| Efficiency | Inefficient efforts; many uncertain movements; constantly changing focus or persisting without progress | | Slow, but planned movements are reasonably organized | | Confident, efficient, and safe conduct, maintains focus on task, fluid progression |
| Force sensitivity | Rough moves, tears tissue, injures nearby structures, poor control, frequent suture breakage | | Handles tissues reasonably well, minor trauma to adjacent tissue, rare suture breakage | | Applies appropriate tension, negligible injury to adjacent structures, no suture breakage |
| Robotic control | Consistently does not optimize view, hand position, or repeated collisions even with guidance | | View is sometimes not optimal. Occasionally needs to relocate arms. Occasional collisions and obstruction of assistant. | | Controls camera and hand position optimally and independently. Minimal collisions or obstruction of assistant. |

*FIG. 16*

AUTOMATED ASSESSMENT OF OPERATOR PERFORMANCE

TECHNICAL FIELD

The present disclosure relates generally to the assessment of a performance of an activity, and more particularly, but not exclusively, to deploying artificial intelligence to assess and normalize assessment content associated with a performance of the activity.

BACKGROUND

Assessing the performance of an individual or team or group of individuals is beneficial or required in many healthcare related professions and the like. For instance, the training of individuals or groups to enter into some healthcare fields requires lengthy cycles of the individuals or groups practicing activities related to the fields as well as teachers, trainers, mentors, or other individuals who have already mastered the activity (an expert) to assess the individuals or groups. Even after the lengthy training period, certain healthcare professions require an on-going assessment of the individual's or group's competency to perform certain activities related to the field. In some of these healthcare professions, the availability of experts to observe and assess the performance of others is limited. Furthermore, the cost associated with an healthcare expert assessing the performance of others may be prohibitively expensive. Finally, even if availability and cost challenges are overcome, expert peer review, which is often unblinded, can yield biased and inaccurate results.

Additionally, these many healthcare activities often involve high-value endeavors, such that seemingly small failure rates can have significant financial and human costs. While human teaching, training, and mentoring can go a long way to improving results in these fields, causes of error still may elude human detection. Furthermore, even if humans are able to detect potential causes of error, practical concerns such as prioritizing areas of improvement, convincing a practitioner of a need to improve, and identifying means of improvement, pose additional challenges. It is for these and other concerns that the following disclosure is offered.

BRIEF DESCRIPTION OF THE DRAWINGS

FIG. 16 illustrates a logical or functional representation of a data model for representing assessment scores for one or more portions or steps of assessed procedures in accordance with one or more of the various embodiments.

DETAILED DESCRIPTION OF THE INVENTION

Figure 1:
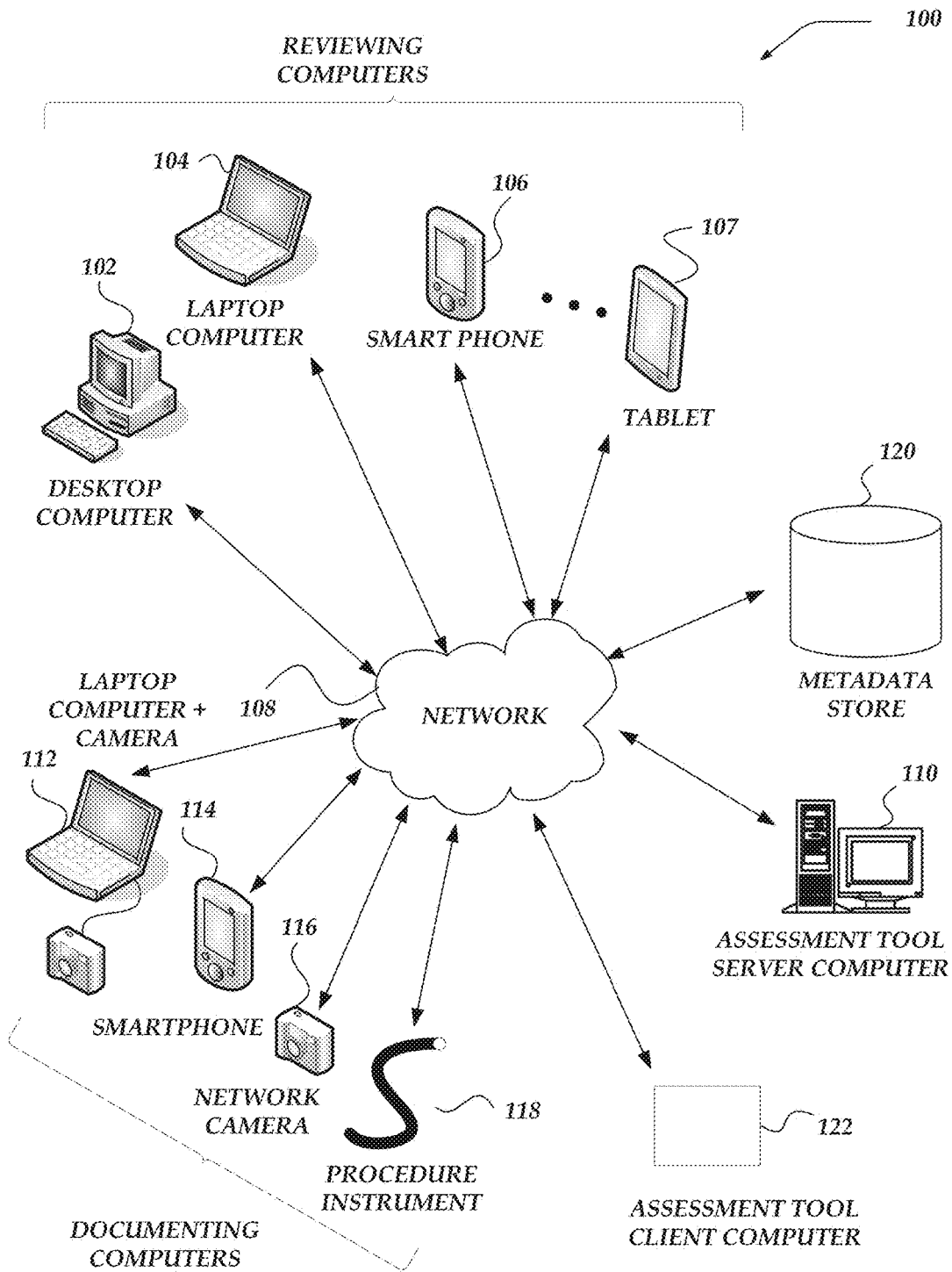
FIG. 1 is a system diagram of an environment in which embodiments of the invention may be implemented.

Various embodiments are described more fully hereinafter with reference to the accompanying drawings, which form a part hereof, and which show, by way of illustration, specific embodiments by which the invention may be practiced. The embodiments may, however, be embodied in many different forms and should not be construed as limited to the embodiments set forth herein; rather, these embodiments are provided so that this disclosure will be thorough and complete, and will fully convey the scope of the embodiments to those skilled in the art. Among other things, the various embodiments may be methods, systems, media, or devices. Accordingly, the various embodiments may be entirely hardware embodiments, entirely software embodiments, or embodiments combining software and hardware aspects. The following detailed description should, therefore, not be limiting.

Throughout the specification and claims, the following terms take the meanings explicitly associated herein, unless the context clearly dictates otherwise. The term "herein" refers to the specification, claims, and drawings associated with the current application. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on." As used herein, the term "subject" may refer to any individual human or a plurality of humans, as well as one or more robots, machines, or any other autonomous, or semi-autonomous apparatus, device, or the like, where the various embodiments are directed to an assessment of the subject's performance of an activity. In addition, as used herein, the terms "subject activity," or "activity" may refer to any activity, including but not limited to physical activities, mental activities, machine and/or robotic activities, and other types of activities, such as writing, speaking, manufacturing activities, athletic performances, and the like. The physical activity may be performed by, or controlled by a subject, where the various embodiments are directed to the assessment of the performance of the subject activity by the subject. Many of the embodiments discussed herein refer to an activity performed by a human, although the embodiments are not so constrained. As such, in other embodiments, an activity is performed by a machine, a robot, or the like. The performance of these activities may also be assessed by the various embodiments disclosed herein.

As used herein, the term "performance content" may refer to any data that documents the performance of the subject activity by the subject. For instance, content may include, but is not limited to image data, including still image data and/or video image data, audio data, textual data, and the like. Accordingly, content may be image content, video content, audio content, textual content, and the like.

As used herein, the term "expert reviewer" may refer to an individual that has acquired, either through specialized education, experience, and/or training, a level of expertise in regards to the subject activity. An expert reviewer may be qualified to assessment content documenting the subject activity and provide an assessment to aspects or domains of the subject activity that require expert-level judgement. An expert reviewer may be a peer of the subject or may have a greater level of experience and expertise in the subject activity, as compared to the subject. An expert reviewer may be known to the subject or may be completely anonymous.

As used herein, the term "crowd reviewer" may be a layperson that has no or minimal specialized education, experience, and/or training in regards to the subject activity. A crowd reviewer may be qualified to assessment content documenting the subject activity and provide an assessment to aspects or domains of the subject activity that do not require expert-level judgement. A crowd reviewer may be trained by the embodiments discussed herein to develop or increase their experience in evaluating various subject performances.

As used herein, the terms "technical aspect" or "technical domains" may refer to aspects or domains of the subject activity that may be reviewed and assessed by a crowd reviewer and/or an expert reviewer. As used herein, the terms "non-technical aspect" or "non-technical domains" may refer to aspects or domains of the subject activity that require an expert-level judgement to review and assess. Accordingly, an expert reviewer is qualified to review and assess non-technical aspects or domains of the performance of the subject activity. In contrast, a crowd reviewer may not be inherently qualified to review and assess non-technical aspects or domains of the performance of the subject activity. However, embodiments are not so constrained, and a crowd reviewer may be qualified to assess non-technical aspects of domains, such as but not limited to provider-patient interactions, bedside manner, and the like. As used herein, the term "assessment content" refers to an assessment of an activity or sub-activity (e.g., step) created by a reviewer. Assessment content may be created in real-time while one or more reviewers observe an activity, or post hoc based on recorded performance content. Assessment content may be unstructured data, such as, text, voice dictation, or the like. Assessment content may include some structured or semi-structure data such as form based survey responses. Also, in some embodiments, assessment content may be machine generated by one or more apparatuses arranged to measure or evaluate activities or sub-activities. In some cases, assessment content may be correlated with a point in time, such as an amount of time elapsed from the beginning of the activity, such that portions of the assessment content may later be associated with the activity or sub-activity taking place at that point in time.

Briefly stated, embodiments are directed to assessing performances of physical activities. In one or more of the various embodiments, one or more assessment engines may be employed to various perform actions described in more detail below.

In one or more of the various embodiments, assessment engines may collect performance content that includes information associated with one or more performances of one or more activities. In some embodiments, collecting the performance content may include receiving a video stream of an activity performed by one or more subjects and generating the assessment content based on the one or more performances included in the video stream.

In one or more of the various embodiments, the assessment engines may employ one or more classifiers to classify the performance content to determine one or more occurrences of one or more features of the performance content and classify assessment content to determine one or more scores that are associated with one or more features included in the one or more performances, such that the assessment content includes information associated with one or more features of the one or more performances of the one or more activities.

In one or more of the various embodiments, providing the one or more correlation values associated with the one or more performances may include: receiving a timeline that defines one or more steps that comprise the one or more activities; correlating the one or more performances with the timeline based on occurrence of the one or more steps; and modifying the one or more classifiers based on the correlation of the one or more performances with the timeline.

In one or more of the various embodiments, classifying the assessment content may include: classifying unstructured content that is provided by different sources; and further determining the one or more scores based on the classification of the unstructured content.

In one or more of the various embodiments, the assessment engines may provide one or more correlation values associated with the one or more performances based on historical performance content, assessment content, and scores.

In one or more of the various embodiments, the assessment engine may provide a report that includes a localized evaluation of the one or more performances based on the correlation values, performance content, assessment content, and scores.

In one or more of the various embodiments, the assessment engine may provide real-time feedback to one or more subjects that may be performing the one or more activities.

Accordingly, one or more responses from the one or more subjects that are associated with the real-time feedback may be collected.

In one or more of the various embodiments, the assessment engine may be arranged to update the one or more classifiers based on the one or more correlation values.

In one or more of the various embodiments, the assessment engine may be arranged to extract a portion of the performance content associated with the assessment content based on the one or more scores that exceed a defined value. Accordingly, the assessment engine may be arranged to provide the extracted portion of the performance content and its assessment content to a classification processing engine for use as training data.

Illustrated Operating Environment

FIG. 1 shows a system diagram of an environment 100 in which embodiments of the invention may be implemented. Not all of the components may be required to practice the various embodiments, and variations in the arrangement and type of the components may be made without departing from the spirit or scope of the invention. As shown, system 100 of FIG. 1 may include assessment tool server computer (ATSC) 110, metadata store 120, reviewing computers 102-107, documenting computers 112-118, assessment tool client computer 122, and network 108. In at least one of the various embodiments, one or more of the above-referenced computing devices may be implemented using one or more cloud instances in one or more cloud networks. Accordingly, these innovations and embodiments are not to be construed as being limited to a single environment, and other configurations, and architectures are also envisaged.

Various embodiments of documenting computers 112-118 or assessment tool client computer 122 are configured to communicate with at least ATSC 110. In various embodiments, one or more documenting computers 112-118 or assessment tool client computer 122 may be enabled to capture content that documents human activity. The content may be image content, including but not limited to video content. In at least one embodiment, the content includes audio content. In at least some embodiments, one or more documenting computers 112-118 may include or be included in various industry-specific or proprietary systems. For instance, one of documenting computers 112-118, as well as a storage device, may be included in a surgical robot, such as but not limited to a da Vinci Surgical System™ from Intuitive Surgical™. In at least one of the various embodiments, a user of one of reviewing computers 102-107 may be enabled to generate commentary regarding the procedures recorded by documenting computer 112-118. Additionally or alternatively, a user of the documenting computers 112-118 may make suggestions, such as trim, timestamp, annotation, and/or tag to be forwarded to ATSC 110.

In at least one of various embodiments, documenting computers 112-118 or assessment tool client computer 122 may be enabled to capture content documenting human activity via image sensors, cameras, microphones, and the like. Documenting computers 112-118 or assessment tool client computer 122 may be enabled to communicate (e.g., via a Bluetooth or other wireless technology, or via a USB cable or other wired technology) with a camera. In some embodiments, at least some of documenting computers 112-118 may operate over a wired and/or wireless network, including network 108, to communicate with other computing devices, including any of reviewing computers 102-107 and/or ATSC 110.

Generally, documenting computers 112-118 or assessment tool client computer 122 may include computing devices capable of communicating over a network to send and/or receive information, perform various online and/or offline activities, or the like. It should be recognized that embodiments described herein are not constrained by the number or type of documenting computers employed, and more or fewer documenting computers—and/or types of documenting computers—than what is illustrated in FIG. 1 may be employed. At least one documenting computer 112-118 may be a client computer.

Devices that may operate as documenting computers 112-118 or assessment tool client computer 122 may include various computing devices that typically connect to a network or other computing device using a wired and/or wireless communications medium. Documenting computers 112-118 may include mobile devices, portable computers, and/or non-portable computers. Examples of non-portable computers may include, but are not limited to, desktop computers, personal computers, multiprocessor systems, microprocessor-based or programmable electronic devices, network PCs, or the like, or integrated devices combining functionality of one or more of the preceding devices. Examples of portable computers may include, but are not limited to, laptop computer 112. Laptop computer 112 is communicatively coupled to a camera via a Universal Serial Bus (USB) cable or some other (wired or wireless) bus capable of transferring data. Examples of mobile computers include, but are not limited to, smart phone 114, tablets, cellular telephones, display pagers, Personal Digital Assistants (PDAs), handheld computers, wearable computing devices, or the like, or integrated devices combining functionality of one or more of the preceding devices. Documenting computers may include a networked computer, such as networked camera 116. Documenting computers may also include, or be connected to, a procedure instrument utilized to perform the procedure being captured, such as procedure instrument 118, a GoPro®, a body cam, and the like. As such, documenting computers 112-118 may include computers with a wide range of capabilities and features.

Documenting computers 112-118 or assessment tool client computer 122 may access and/or employ various computing applications to enable users to perform various online and/or offline activities. Such activities may include, but are not limited to, generating documents, gathering/monitoring data, capturing/manipulating images/videos, managing media, managing financial information, playing games, managing personal information, browsing the Internet, or the like. In some embodiments, documenting computers 112-118 or assessment tool client computer 122 may be enabled to connect to a network through a browser, or other web-based application.

Documenting computers 112-118 or assessment tool client computer 122 may further be configured to provide information that identifies the documenting computer. Such identifying information may include, but is not limited to, a type, capability, configuration, name, or the like, of the documenting computer. In at least one embodiment, a documenting computer may uniquely identify itself through any of a variety of mechanisms, such as an Internet Protocol (IP) address, phone number, Mobile Identification Number (MIN), media access control (MAC) address, electronic serial number (ESN), or other device identifier.

Various embodiments of reviewing computers 102-107 are described in more detail below in conjunction with Client computer 200 of FIG. 2. Briefly, in some embodiments, at least one of the reviewing computers 102-107 may be configured to communicate with ATSC 110. In various embodiments, one or more reviewing computers 102-107 may be enabled to access, interact with, and/or view live or recorded streaming content from ATSC 110, such as through a web browser. In at least one of various embodiments, a user of a reviewing computer may be enabled to assessment content provided by ATSC 110. The user may be enabled to provide commentary, written or verbal, to ATSC 110.

Generally, documenting computers 102-107 may include computing devices capable of communicating over a network to send and/or receive information, perform various online and/or offline activities, or the like. It should be recognized that embodiments described herein are not constrained by the number or type of reviewing computers employed, and more or fewer reviewing computers—and/or types of reviewing computers—than what is illustrated in FIG. 1 may be employed. At least one reviewing computer 102-107 may be a client computer.

Devices that may operate as reviewing computers 102-107 may include various computing devices that typically connect to a network or other computing device using a wired and/or wireless communications medium. Reviewing computers 102-107 may include mobile devices, portable computers, and/or non-portable computers. Examples of non-portable computers may include, but are not limited to, desktop computers 102, personal computers, multiprocessor systems, microprocessor-based or programmable electronic devices, network PCs, or the like, or integrated devices combining functionality of one or more of the preceding devices. Examples of portable computers may include, but are not limited to, laptop computer 104. Examples of mobile computers include, but are not limited to, smart phone 106, tablet computer 107, cellular telephones, display pagers, Personal Digital Assistants (PDAs), handheld computers, wearable computing devices, or the like, or integrated devices combining functionality of one or more of the preceding devices. As such, documenting computers 102-107 may include computers with a wide range of capabilities and features.

Reviewing computers 102-107 may access and/or employ various computing applications to enable users to perform various online and/or offline activities. Such activities may include, but are not limited to, generating documents, gathering/monitoring data, capturing/manipulating images, reviewing content, managing media, managing financial information, playing games, managing personal information, browsing the Internet, or the like. In some embodiments, reviewing computers 102-107 may be enabled to connect to a network through a browser, or other web-based application.

Reviewing computers 102-107 may further be configured to provide information that identifies the reviewing computer. Such identifying information may include, but is not limited to, a type, capability, configuration, name, or the like, of the reviewing computer. In at least one embodiment, a reviewing computer may uniquely identify itself through any of a variety of mechanisms, such as an Internet Protocol (IP) address, phone number, Mobile Identification Number (MIN), media access control (MAC) address, electronic serial number (ESN), or other device identifier.

Various embodiments of ATSC 110 are described in more detail below in conjunction with network computer 300 of FIG. 3. Briefly, in some embodiments, ATSC 110 may be operative to receive video captured by documenting computers 112-118 or assessment tool client computer 122, provide the video to and solicit commentary from reviewing computers 102-107, tokenize the commentary into sentences, classify the sentences as positive, neutral, or negative, aggregate the classification results, and store the classification results on metadata store 120. In some embodiments, an assessment tool client computer, such assessment tool client computer 122 may be arranged to collect or capture procedure data that may later or in real-time provided to ATSC 110. ATSC 110 may, additionally or alternatively, be operative to classify the recorded video to identify pertinent events in the course of the activity. For example, in the field of surgery, events such as bleeding, cautery, smoke, suturing, body parts, and the like may be identified. ATSC 110 may also perform a higher level analysis. Continuing the example of surgery, ATSC may detect whether a camera recording the video is inside or outside the body, whether suturing has approximated the tissue well (neither too tight or too loose), whether cauterizing is sufficient to keep the surgical field free of excess blood, and other surgical procedures.

Various embodiments of ATSC 110 may then process, make available, and act on the classification information. For example, ATSC 110 may process aggregate classification information (including classification information retrieved from metadata store 120), to identify trends, patterns, exceptions, or correlations or relationships to other data (e.g. which data elements most influence surgeon performance and/or patient outcomes). ATSC may make this information available through, for example, a website, allowing access to relevant portions of commentary received from reviewing computers 102-107, insights realized by direct classification of the video, or comparisons to other data elements, including those pertaining to other media or surgeon performances. Furthermore, ATSC may be integrated with a scheduling system to help assign future tasks. Continuing the surgery example, if a set of upcoming surgical procedures are to be scheduled, ATSC 110 may provide data on efficiency and effectiveness of different surgeons, enabling a more optimal assignment of surgeons to tasks they are capable of completing effectively.

Network 108 may include virtually any wired and/or wireless technology for communicating with a remote device, such as, but not limited to, USB cable, Bluetooth, Wi-Fi, or the like. In some embodiments, network 108 may be a network configured to couple network computers with other computing devices, including reviewing computers 102-107, documenting computers 112-118, or assessment tool client computer 122, assessment tool server computer 110, assessment tool client computer 122, metadata store 120, and the like. In various embodiments, information communicated between devices may include various kinds of information, including, but not limited to, processor-readable instructions, remote requests, server responses, program modules, applications, raw data, control data, system information (e.g., log files), video data, voice data, image data, text data, structured/unstructured data, or the like. In some embodiments, this information may be communicated between devices using one or more technologies and/or network protocols.

In some embodiments, such a network may include various wired networks, wireless networks, or any combination thereof. In various embodiments, the network may be enabled to employ various forms of communication technology, topology, computer-readable media, or the like, for communicating information from one electronic device to another. For example, the network can include—in addition to the Internet—LANs, WANs, Personal Area Networks (PANs), Campus Area Networks, Metropolitan Area Networks (MANs), direct communication connections (such as through a universal serial bus (USB) port), or the like, or any combination thereof.

In various embodiments, communication links within and/or between networks may include, but are not limited to, twisted wire pair, optical fibers, open air lasers, coaxial cable, plain old telephone service (POTS), wave guides, acoustics, full or fractional dedicated digital lines (such as T1, T2, T3, or T4), E-carriers, Integrated Services Digital Networks (ISDNs), Digital Subscriber Lines (DSLs), wireless links (including satellite links), or other links and/or carrier mechanisms known to those skilled in the art. Moreover, communication links may further employ any of a variety of digital signaling technologies, including without limit, for example, DS-0, DS-1, DS-2, DS-3, DS-4, OC-3, OC-12, OC-48, or the like. In some embodiments, a router (or other intermediate network device) may act as a link between various networks—including those based on different architectures and/or protocols—to enable information to be transferred from one network to another. In other embodiments, remote computers and/or other related electronic devices could be connected to a network via a modem and temporary telephone link. In essence, the network may include any communication technology by which information may travel between computing devices.

The network may, in some embodiments, include various wireless networks, which may be configured to couple various portable network devices, remote computers, wired networks, other wireless networks, or the like. Wireless networks may include any of a variety of sub-networks that may further overlay stand-alone ad-hoc networks, or the like, to provide an infrastructure-oriented connection for at least reviewing computers 102-107, documenting computers 112-118, or assessment tool client computer 122, or the like. Such sub-networks may include mesh networks, Wireless LAN (WLAN) networks, cellular networks, or the like. In at least one of the various embodiments, the system may include more than one wireless network.

The network may employ a plurality of wired and/or wireless communication protocols and/or technologies. Examples of various generations (e.g., third (3G), fourth (4G), or fifth (5G)) of communication protocols and/or technologies that may be employed by the network may include, but are not limited to, Global System for Mobile communication (GSM), General Packet Radio Services (GPRS), Enhanced Data GSM Environment (EDGE), Code Division Multiple Access (CDMA), Wideband Code Division Multiple Access (W-CDMA), Code Division Multiple Access 2000 (CDMA2000), High Speed Downlink Packet Access (HSDPA), Long Term Evolution (LTE), Universal Mobile Telecommunications System (UMTS), Evolution-Data Optimized (Ev-DO), Worldwide Interoperability for Microwave Access (WiMax), time division multiple access (TDMA), Orthogonal frequency-division multiplexing (OFDM), ultra wide band (UWB), Wireless Application Protocol (WAP), user datagram protocol (UDP), transmission control protocol/Internet protocol (TCP/IP), any portion of the Open Systems Interconnection (OSI) model protocols, session initiated protocol/real-time transport protocol (SIP/RTP), short message service (SMS), multimedia messaging service (MMS), or any of a variety of other communication protocols and/or technologies. In essence, the network may include communication technologies by which information may travel between reviewing computers 102-107, documenting computers 112-118, or assessment tool client computer 122, ATSC 110, metadata store 120, other computing devices not illustrated, other networks, and the like.

In various embodiments, at least a portion of the network may be arranged as an autonomous system of nodes, links, paths, terminals, gateways, routers, switches, firewalls, load balancers, forwarders, repeaters, optical-electrical converters, or the like, which may be connected by various communication links. These autonomous systems may be configured to self organize based on current operating conditions and/or rule-based policies, such that the network topology of the network may be modified.

Illustrative Client Computer

Figure 2:
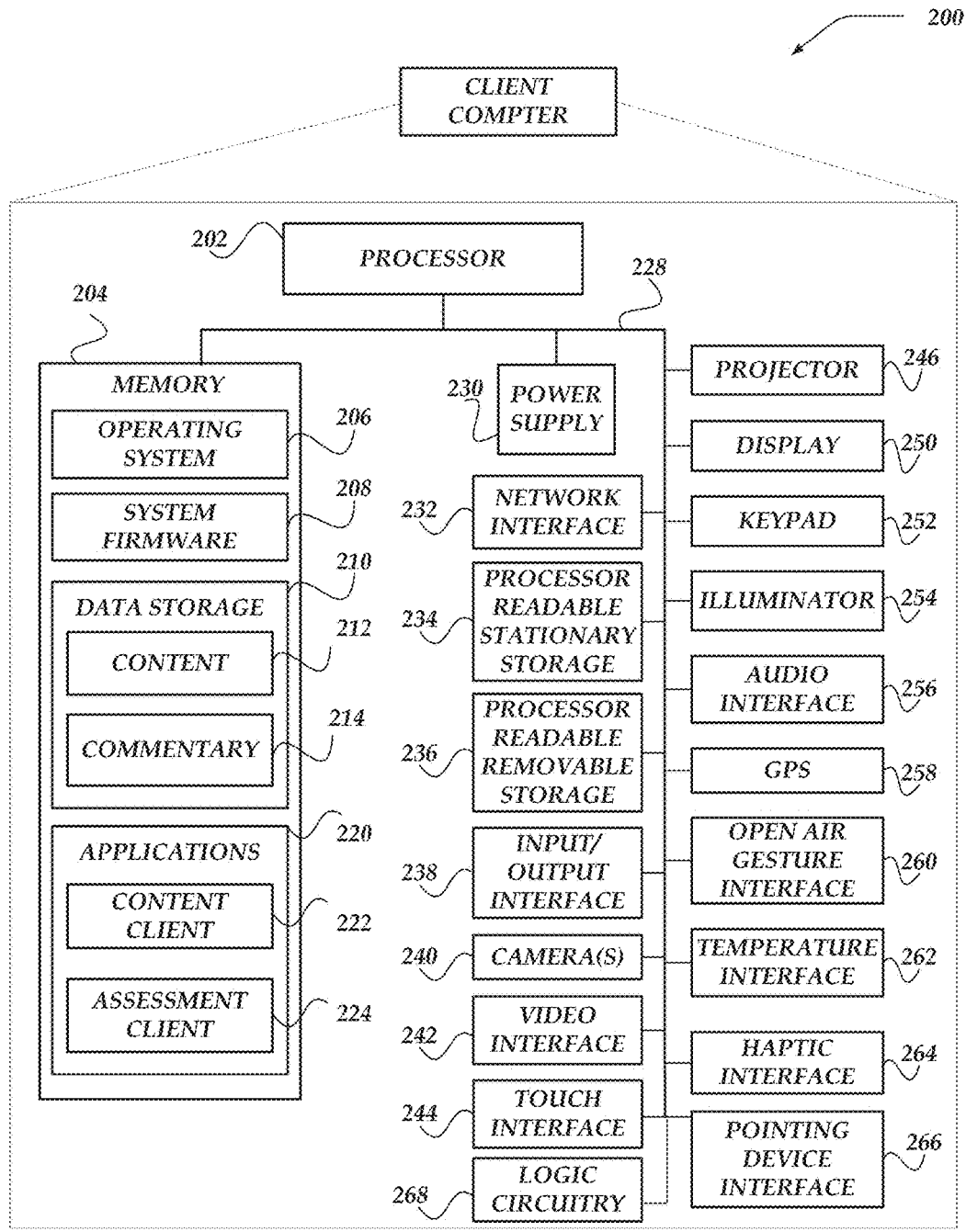
FIG. 2 shows an embodiment of a client computer that may be included in a system such as that shown in FIG. 1.

FIG. 2 shows an embodiment of a client computer 200 that may be included in a system such as that shown in FIG. 1. Client computer 200 may represent, for example, at least one embodiment of documenting computers 112-118, reviewing computers 102-107, assessment tool client computer 122, or the like. Also, client computer 200 may be a mobile device (e.g., a smart phone or tablet), a stationary/desktop computer, or the like.

Client computer 200 may include processor 202, such as a central processing unit (CPU), in communication with memory 204 via bus 228. Client computer 200 may also include power supply 230, network interface 232, processor-readable stationary storage device 234, processor-readable removable storage device 236, input/output interface 238, camera(s) 240, video interface 242, touch interface 244, projector 246, display 250, keypad 252, illuminator 254, audio interface 256, global positioning systems (GPS) receiver 258, open air gesture interface 260, temperature interface 262, haptic interface 264, pointing device interface 266, or the like. Client computer 200 may optionally communicate with a base station (not shown), or directly with another computer. And in one embodiment, although not shown, an accelerometer or gyroscope may be employed within Client computer 200 to measuring and/or maintaining an orientation of Client computer 200.

Additionally, in one or more embodiments, the Client computer 200 may include logic circuitry 268. Logic circuitry 268 may be an embedded logic hardware device in contrast to or in complement to processor 202. The embedded logic hardware device would directly execute its embedded logic to perform actions, e.g., an Application Specific Integrated Circuit (ASIC), Field Programmable Gate Array (FPGA), and the like.

Also, in one or more embodiments (not shown in the figures), the mobile computer may include a hardware microcontroller instead of a CPU. In at least one embodiment, the microcontroller would directly execute its own embedded logic to perform actions and access it's own internal memory and it's own external Input and Output Interfaces (e.g., hardware pins and/or wireless transceivers) to perform actions, such as System On a Chip (SOC), and the like.

Power supply 230 may provide power to Client computer 200. A rechargeable or non-rechargeable battery may be used to provide power. The power may also be provided by an external power source, such as an AC adapter or a powered docking cradle that supplements and/or recharges the battery.

Network interface 232 includes circuitry for coupling Client computer 200 to one or more networks, and is constructed for use with one or more communication protocols and technologies including, but not limited to, protocols and technologies that implement any portion of the OSI model, GSM, CDMA, time division multiple access (TDMA), UDP, TCP/IP, SMS, MMS, GPRS, WAP, UWB, WiMax, SIP/RTP, GPRS, EDGE, WCDMA, LTE, UMTS, OFDM, CDMA2000, EV-DO, HSDPA, or any of a variety of other wireless communication protocols. Network interface 232 is sometimes known as a transceiver, transceiving device, or network interface card (NIC).

Audio interface 256 may be arranged to produce and receive audio signals such as the sound of a human voice. For example, audio interface 256 may be coupled to a speaker and microphone (not shown) to enable telecommunication with others and/or generate an audio acknowledgement for some action. A microphone in audio interface 256 can also be used for input to or control of Client computer 200, e.g., using voice recognition, detecting touch based on sound, and the like. A microphone may be used to capture content documenting the performance of a subject activity.

Display 250 may be a liquid crystal display (LCD), gas plasma, electronic ink, light emitting diode (LED), Organic LED (OLED) or any other type of light reflective or light transmissive display that can be used with a computer. Display 250 may also include a touch interface 244 arranged to receive input from an object such as a stylus or a digit from a human hand, and may use resistive, capacitive, surface acoustic wave (SAW), infrared, radar, or other technologies to sense touch and/or gestures.

Projector 246 may be a remote handheld projector or an integrated projector that is capable of projecting an image on a remote wall or any other reflective object such as a remote screen.

Video interface 242 may be arranged to capture video images, such as a still photo, a video segment, an infrared video, or the like. For example, video interface 242 may be coupled to a digital video camera, a web-camera, or the like. Video interface 242 may comprise a lens, an image sensor, and other electronics. Image sensors may include a complementary metal-oxide-semiconductor (CMOS) integrated circuit, charge-coupled device (CCD), or any other integrated circuit for sensing light.

Keypad 252 may comprise any input device arranged to receive input from a user. For example, keypad 252 may include a push button numeric dial, or a keyboard. Keypad 252 may also include command buttons that are associated with selecting and sending images.

Illuminator 254 may provide a status indication and/or provide light. Illuminator 254 may remain active for specific periods of time or in response to events. For example, when illuminator 254 is active, it may backlight the buttons on keypad 252 and stay on while the mobile device is powered. Also, illuminator 254 may backlight these buttons in various patterns when particular actions are performed, such as dialing another mobile computer. Illuminator 254 may also cause light sources positioned within a transparent or translucent case of the mobile device to illuminate in response to actions.

Client computer 200 may also comprise input/output interface 238 for communicating with external peripheral devices or other computers such as other mobile computers and network computers. Input/output interface 238 may enable Client computer 200 to communicate with one or more servers, such as ATSC 110 of FIG. 1. In some embodiments, input/output interface 238 may enable Client computer 200 to connect and communicate with one or more network computers, such as documenting computers 112-118 and reviewing computers 102-107 of FIG. 1. Other peripheral devices that Client computer 200 may communicate with may include remote speakers and/or microphones, headphones, display screen glasses, or the like. Input/output interface 238 can utilize one or more technologies, such as Universal Serial Bus (USB), Infrared, Wi-Fi, WiMax, Bluetooth™, wired technologies, or the like.

Haptic interface 264 may be arranged to provide tactile feedback to a user of a Client computer 200. For example, the haptic interface 264 may be employed to vibrate Client computer 200 in a particular way when another user of a computer is calling. Temperature interface 262 may be used to provide a temperature measurement input and/or a temperature changing output to a user of Client computer 200. Open air gesture interface 260 may sense physical gestures of a user of Client computer 200, for example, by using single or stereo video cameras, radar, a gyroscopic sensor inside a computer held or worn by the user, or the like. Camera 240 may be used to track physical eye movements of a user of Client computer 200. Camera 240 may be used to capture content documenting the performance of subject activity.

GPS transceiver 258 can determine the physical coordinates of Client computer 200 on the surface of the Earth, which typically outputs a location as latitude and longitude values. Physical coordinates of a mobile computer that includes a GPS transceiver may be referred to as geo-location data. GPS transceiver 258 can also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of Client computer 200 on the surface of the Earth. It is understood that under different conditions, GPS transceiver 258 can determine a physical location for Client computer 200. In at least one embodiment, however, Client computer 200 may, through other components, provide other information that may be employed to determine a physical location of the mobile computer, including for example, a Media Access Control (MAC) address, IP address, and the like. In at least one embodiment, GPS transceiver 258 is employed for localization of the various embodiments discussed herein. For instance, the various embodiments may be localized, via GPS transceiver 258, to customize the linguistics, technical parameters, time zones, configuration parameters, units of measurement, monetary units, and the like based on the location of a user of Client computer 200.

Human interface components can be peripheral devices that are physically separate from Client computer 200, allowing for remote input and/or output to Client computer 200. For example, information routed as described here through human interface components such as display 250 or keyboard 252 can instead be routed through network interface 232 to appropriate human interface components located remotely. Examples of human interface peripheral components that may be remote include, but are not limited to, audio devices, pointing devices, keypads, displays, cameras, projectors, and the like. These peripheral components may communicate over a Pico Network such as Bluetooth™, Zigbee™ and the like. One non-limiting example of a mobile computer with such peripheral human interface components is a wearable computer, which might include a remote pico projector along with one or more cameras that remotely communicate with a separately located mobile computer to sense a user's gestures toward portions of an image projected by the pico projector onto a reflected surface such as a wall or the user's hand.

A Client computer 200 may include a browser application that is configured to receive and to send web pages, web-based messages, graphics, text, multimedia, and the like. Mobile computer's 200 browser application may employ virtually any programming language, including a wireless application protocol messages (WAP), and the like. In at least one embodiment, the browser application is enabled to employ Handheld Device Markup Language (HDML), Wireless Markup Language (WML), WMLScript, JavaScript, Standard Generalized Markup Language (SGML), HyperText Markup Language (HTML), eXtensible Markup Language (XML), HTML5, and the like.

In various embodiments, the browser application may be configured to enable a user to log into an account and/or user interface to access/view content data. In at least one of various embodiments, the browser may enable a user to view reports of assessment data that is generated by ATSC server 110 of FIG. 1. In some embodiments, the browser/user interface may enable the user to customize a view of the report and to receive prescriptive recommendations for personal improvement (e.g., prescriptive improvement) based upon their assessment data. As described herein, the extent to which a user can customize the reports may depend on permissions/restrictions for that particular user.

In various embodiments, the user interface may present the user with one or more web interfaces for capturing content documenting a performance. In some embodiments, the user interface may present the user with one or more web interfaces for reviewing content and assessing a performance of a subject activity.

Memory 204 may include RAM, ROM, and/or other types of memory. Memory 204 illustrates an example of computer-readable storage media (devices) for storage of information such as computer-readable instructions, data structures, program modules or other data. Memory 204 may store system firmware 208 (e.g., BIOS) for controlling low-level operation of Client computer 200. The memory may also store operating system 206 for controlling the operation of Client computer 200. It will be appreciated that this component may include a general-purpose operating system such as a version of UNIX, or LINUX™, or a specialized mobile computer communication operating system such as Windows Phone™, or the Symbian® operating system. The operating system may include, or interface with a Java virtual machine module that enables control of hardware components and/or operating system operations via Java application programs.

Memory 204 may further include one or more data storage 210, which can be utilized by Client computer 200 to store, among other things, applications 220 and/or other data. For example, data storage 210 may store content 212 and/or commentary 214. In the context of documenting computers 112-118, content 212 represents the content captured by a camera (or other input device) to be transmitted to ATSC 110. However, in the context of reviewing computers 102-107, content 212 represents content being reviewed by an expert, enabling the expert to generate commentary 214.

Data storage 210 may further include program code, data, algorithms, and the like, for use by a processor, such as processor 202 to execute and perform actions. In one embodiment, at least some of data storage 210 might also be stored on another component of Client computer 200, including, but not limited to, non-transitory processor-readable removable storage device 236, processor-readable stationary storage device 234, or even external to the mobile device. Removable storage device 236 may be a USB drive, USB thumb drive, dongle, or the like.

Applications 220 may include computer executable instructions which, when executed by Client computer 200, transmit, receive, and/or otherwise process instructions and data. Applications 220 may include content client 222. In the context of documenting computers 112-118, content client 222 may capture, manage, and/or receive content that documents human activity. Applications 220 may include assessment client 224. In the context of reviewing computers 102-107, assessment client 224 may select, display, and solicit feedback from a user, regarding a piece of content.

Other examples of application programs that may be included in applications 220 include, but are not limited to, calendars, search programs, email client applications, IM applications, SMS applications, Voice Over Internet Protocol (VOIP) applications, contact managers, task managers, transcoders, database programs, word processing programs, security applications, spreadsheet programs, games, search programs, and so forth.

Furthermore, in at least one of the various embodiments, applications 220, or the like, may be operative in a cloud-based computing environment. In at least one of the various embodiments, in this context applications may flow from one physical network computer within the cloud-based environment to another depending on performance and scaling considerations automatically managed by the cloud computing environment. Likewise, in at least one of the various embodiments, virtual machines and/or virtual servers may be provisioned and de-commissioned automatically.

So, in some embodiments, Client computer 200 may be enabled to employ various embodiments, combinations of embodiments, processes, or parts of processes, as described herein. Moreover, in various embodiments, Client computer 200 may be enabled to employ various embodiments described above in conjunction with computer device of FIG. 1.

Illustrative Network Computer

Figure 3:
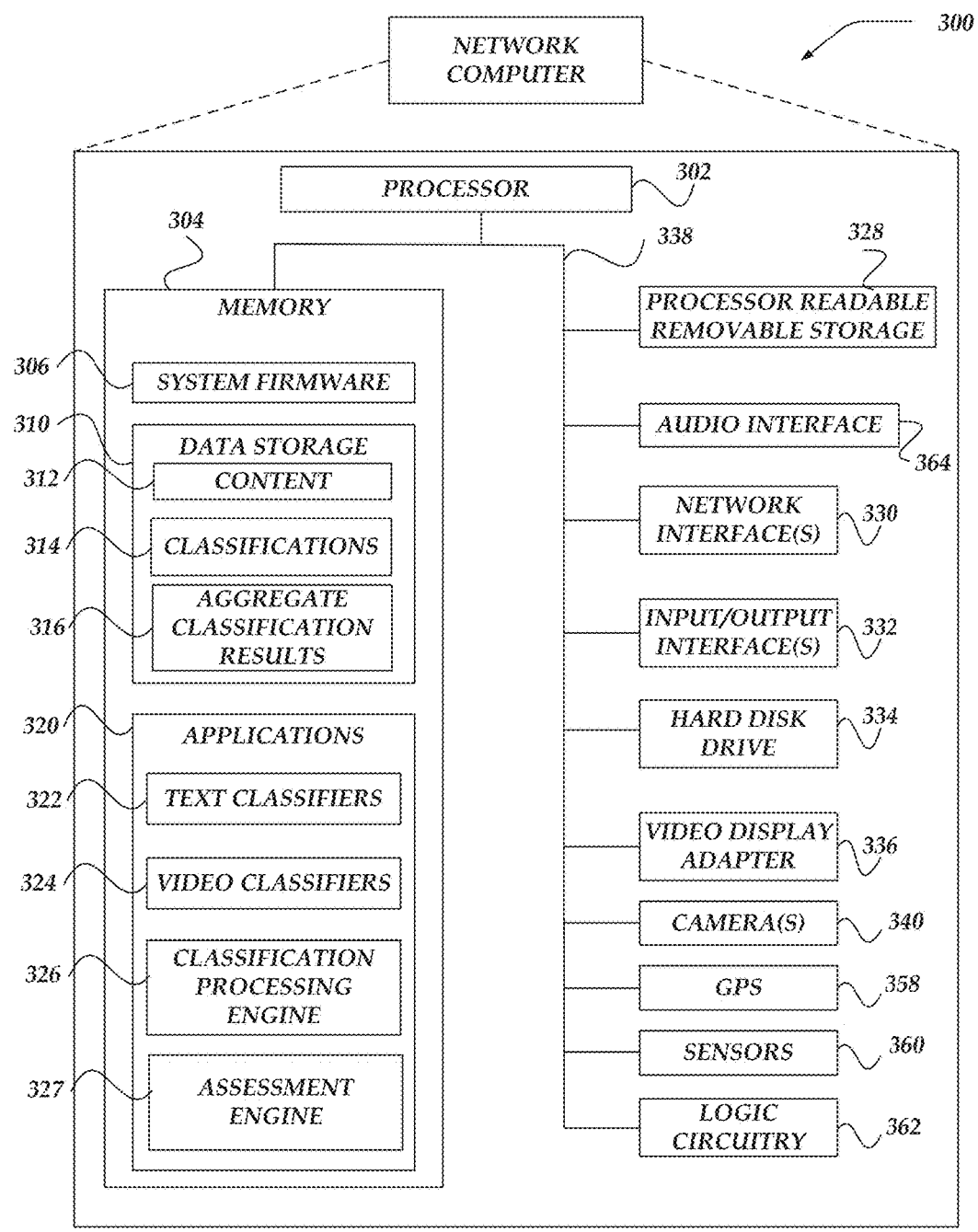
FIG. 3 illustrates an embodiment of a network computer that may be included in a system such as that shown in FIG. 1.

FIG. 3 illustrates an embodiment of a network computer 300 that may be included in a system such as that shown in FIG. 1. Network computer 300 may represent, for example, assessment tool server computer 110. Network computer 300 may be a desktop computer, a laptop computer, a server computer, a client computer, and the like.

Network computer 300 may include processor 302, such as a CPU, processor readable storage media 328, network interface unit 330, an input/output interface 332, hard disk drive 334, video display adapter 336, GPS 338, and memory 304, all in communication with each other via bus 338. In some embodiments, processor 302 may include one or more central processing units.

Additionally, in one or more embodiments (not shown in the figures), the network computer may include an embedded logic hardware device instead of a CPU. The embedded logic hardware device would directly execute its embedded logic to perform actions, e.g., an Application Specific Integrated Circuit (ASIC), Field Programmable Gate Array (FPGA), and the like.

Also, in one or more embodiments (not shown in the figures), the network computer may include a hardware microcontroller instead of a CPU. In at least one embodiment, the microcontroller would directly execute its own embedded logic to perform actions and access it's own internal memory and it's own external Input and Output Interfaces (e.g., hardware pins and/or wireless transceivers) to perform actions, such as System On a Chip (SOC), and the like.

As illustrated in FIG. 3, network computer 300 also can communicate with the Internet, cellular networks, or some other communications network (either wired or wireless), via network interface unit 330, which is constructed for use with various communication protocols. Network interface unit 330 is sometimes known as a transceiver, transceiving device, or network interface card (NIC). In some embodiments, network computer 300 may communicate with a documenting computer, reviewing computer, or a computer included in an ATP platform, or any other network computer, via the network interface unit 330.

Network computer 300 also comprises input/output interface 332 for communicating with external devices, such as a various sensors or other input or output devices not shown in FIG. 3. Input/output interface 332 can utilize one or more communication technologies, such as USB, infrared, Bluetooth™, or the like.

Memory 304 generally includes RAM, ROM and one or more permanent mass storage devices, such as hard disk drive 334, tape drive, optical drive, and/or floppy disk drive. Memory 304 may store system firmware 306 for controlling the low-level operation of network computer 300 (e.g., BIOS). In some embodiments, memory 304 may also store an operating system for controlling the operation of network computer 300.

Although illustrated separately, memory 304 may include processor readable storage media 328. Processor readable storage media 328 may be referred to and/or include computer readable media, computer readable storage media, and/or processor readable storage device. Processor readable removable storage media 328 may include volatile, nonvolatile, removable, and non-removable media implemented in any method or technology for storage of information, such as computer readable instructions, data structures, program modules, or other data. Examples of processor readable storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other media which can be used to store the desired information and which can be accessed by a computing device.

Memory 304 further includes one or more data storage 310, which can be utilized by network computer 300 to store, among other things, content 312, classifications 314, aggregate classification results 316, and/or other data. For example, data storage 310 may further include program code, data, algorithms, and the like, for use by a processor, such as processor 302 to execute and perform actions. In one embodiment, at least some of data storage 310 might also be stored on another component of network computer 300, including, but not limited to processor-readable storage media 328, hard disk drive 334, or the like.

Content data 312 may include content that documents a subject's performance of a subject activity, such as pictures, video, audio, or the like. Classifications 314 may include an output of a machine learning algorithm applied to content data 312. Additionally or alternatively, classifications 314 may include an output of a machine learning algorithm applied to commentary 214. Aggregate classification results 316 may include the result of an analysis applied to classification results. For example, in the context of surgery, aggregate classification results may include when a particular aspect of a procedure has begun, how effective a particular step was (e.g. did cautery sufficiently stop bleeding), etc. Classification results associated with multiple subjects over multiple recording sessions are contemplated, allowing comparison between subjects, advancement or regression of a given subject, or the like, to be reviewed.

Applications 320 may include computer executable instructions that can execute on processor 302 to perform actions. In some embodiments, one or more applications 320 may be part of an application that may be loaded into mass memory and run on an operating system Applications 320 may include text classifiers 322, video classifiers 324, classification processing engine 326, and assessment engine 327. Text classifiers 322 process words, sentences, and/or paragraphs to identify features of written commentary. For example, text classifiers 322 may identify positive, negative, or neutral comments, as well as severity and/or relativity. Video classifiers 324 may identify various events/attributes of the activity recorded in the video. For example, in a surgical context, video classifiers may identify bleeding, cautery, suturing, or other surgical events or techniques. In one embodiment, classifiers refer to machine learning systems, e.g. neural networks that have been trained with a "ground truth" to identify certain features. In the context of surgery, for example, a machine learning system may be trained with videos depicting suturing, along with an indication (i.e. ground truth) that a human expert has identified the videos as including suturing. By applying machine learning techniques, these classifiers process this input, and can then be used to identify, to a level of confidence, the existence of the trained event, e.g. suturing.

Classification processing engine 326, in one embodiment, may analyze the classification results, including by aggregating identified features and comparing, among and between subjects, classifications of the same or different activities. Classification processing engine 326 may also collate reviewer data and/or generate, provide, and/or receive reports based on the reviewer data.

Assessment engine 327, in some embodiments, may control or perform various portions of automated assessment of operator performance, as described in more detail below.

Furthermore, applications 320 may include one or more additional applications. For example, at least a portion of the server applications in applications 320 may at least partially form a data layer of the metadata store 120 of FIG. 1.

GPS transceiver 358 can determine the physical coordinates of network computer 300 on the surface of the Earth, which typically outputs a location as latitude and longitude values. Physical coordinates of a network computer that includes a GPS transceiver may be referred to as geolocation data. GPS transceiver 358 can also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of network computer 300 on the surface of the Earth. It is understood that under different conditions, GPS transceiver 358 can determine a physical location for network computer 300. In at least one embodiment, however, network computer 300 may, through other components, provide other information that may be employed to determine a physical location of the mobile computer, including for example, a Media Access Control (MAC) address, IP address, and the like. In at least one embodiment, GPS transceiver 358 is employed for localization of the various embodiments discussed herein. For instance, the various embodiments may be localized, via GPS transceiver 258, to customize the linguistics, cultural preferences, geographic regional preferences, political preferences, religious preferences, holidays, weather information, disaster information, technical parameters, time zones, configuration parameters, units of measurement, monetary units, and the like based on the location of a user of Client computer 200.

Audio interface 364 may be arranged to produce and receive audio signals such as the sound of a human voice. For example, audio interface 354 may be coupled to a speaker and microphone (not shown) to enable telecommunication with others and/or generate an audio acknowledgement for some action. A microphone in audio interface 364 can also be used for input to or control of network computer 300, e.g., using voice recognition, detecting touch based on sound, and the like. A microphone may be used to capture content documenting the performance of a subject activity. Likewise, camera 340 may be used to capture content documenting the performance of subject activity. Other sensors 360 may be included to sense a location, or other environment component.

Additionally, in one or more embodiments, the network computer 300 may include logic circuitry 362. Logic circuitry 362 may be an embedded logic hardware device in contrast to or in complement to processor 302. The embedded logic hardware device would directly execute its embedded logic to perform actions, e.g., an Application Specific Integrated Circuit (ASIC), Field Programmable Gate Array (FPGA), Tensor Processing Unit (TPU), or the like.

So, in some embodiments, network computer 300 may be enabled to employ various embodiments, combinations of embodiments, processes, or parts of processes, as described herein. Moreover, in various embodiments, network computer 300 may be enabled to employ various embodiments described above in conjunction with computer device of FIG. 1.

Exemplary Embodiments

Figure 4:
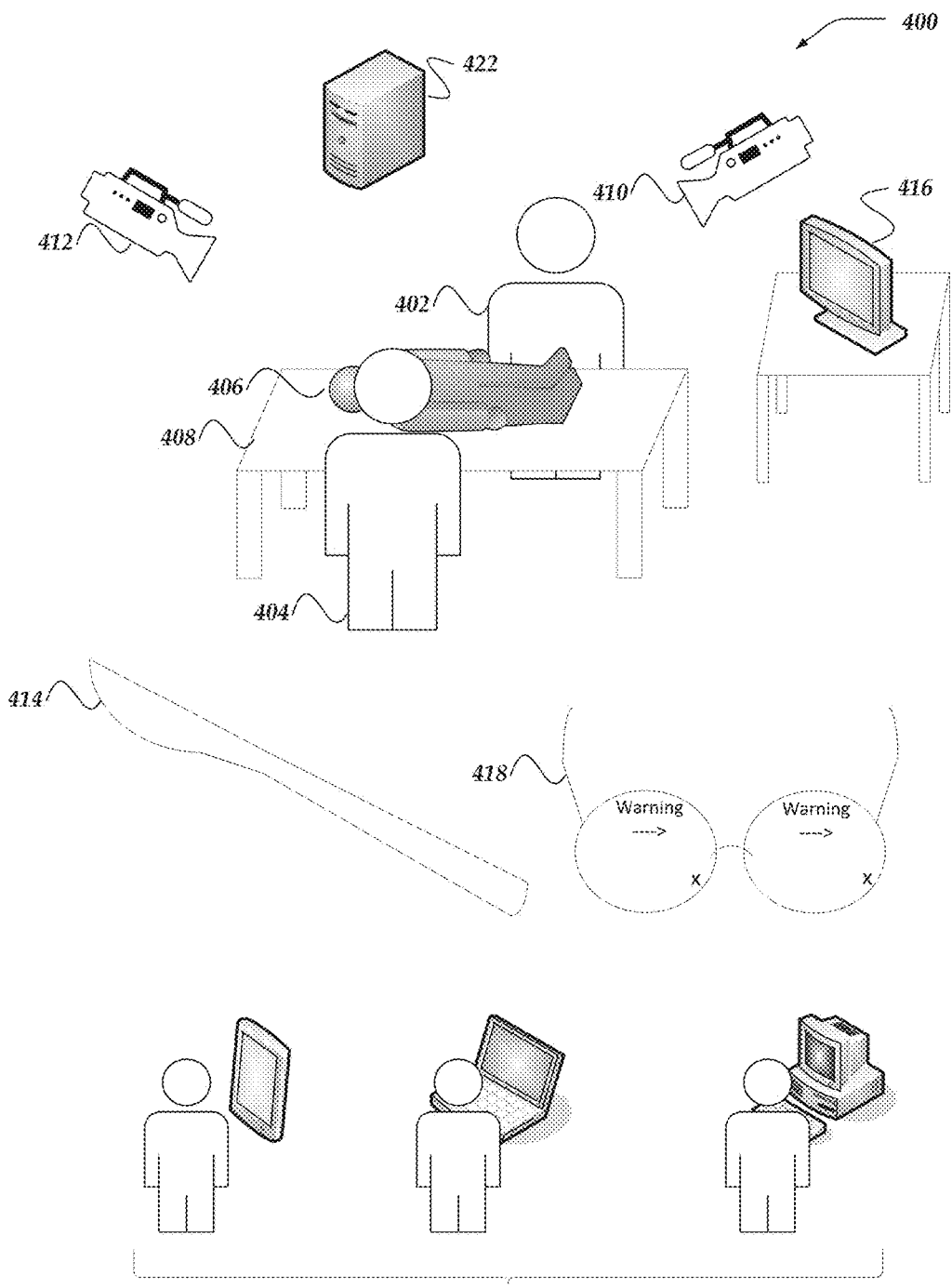
FIG. 4 illustrates one exemplary embodiment of the claimed embodiments.

FIG. 4 illustrates one exemplary embodiment 400 of one or more of the various embodiments. While other types of healthcare related activities are similarly contemplated, such as nursing, dentistry, sonography, or the like, for brevity and clarity FIG. 4 and other embodiments discussed throughout this document refer to surgery and related activities. For example, surgeon 402 and assistant 404 stand in an operating room tending to patient 406 on operating table 408.

In one or more of the various embodiments, the surgical operation is recorded by one or more cameras such as documenting computers 112-118. For example, cameras 410 and/or 412 could be used to create a video of the operation. However, any type of camera is similarly contemplated, such as endoscopic camera 118. In one or more of the various embodiments, video captured by the cameras is forwarded to ATSC 110 for real-time processing, as discussed below, including classification of the video by a machine learning agent. Results of this processing may be transmitted back to the operating room for display on monitor 416 or augmented vision glasses 418, which may alert the surgeon to an impending problem.

In one or more of the various embodiments, classification performed on the video stream includes identification of surgical instruments, such as scalpel 414. By identifying surgical instruments, higher level processing performed by classification processing engine 326 can identify which specific instrument (make, model, version) is being used and by whom, when a surgical instrument is idle, when it is about to cause damage to the patient, and/or when the surgical instrument in use is sub-optimal and should be replaced.

Additionally or alternatively, reviewers 420 generate text or audio based commentary of the recorded surgical procedure. As discussed below, these reviewers may be colleagues, or other surgeons unknown to the person performing the subject procedure. Additionally or alternatively, these reviewers may be assistants or lay people. Reviewers may comment on the operation, either in real-time or based on a recording. In one or more of the various embodiments, these comments are transmitted to ATSC 110 for classification and further processing.

In one or more of the various embodiments, network computer 422 may be a computer or computing appliance that is running a capture engine or capture agent that is used to locally capture performance content as it is being generated. The performance content may be uploaded to a data store for further analysis according to one or more rule based policies.

Figure 5:
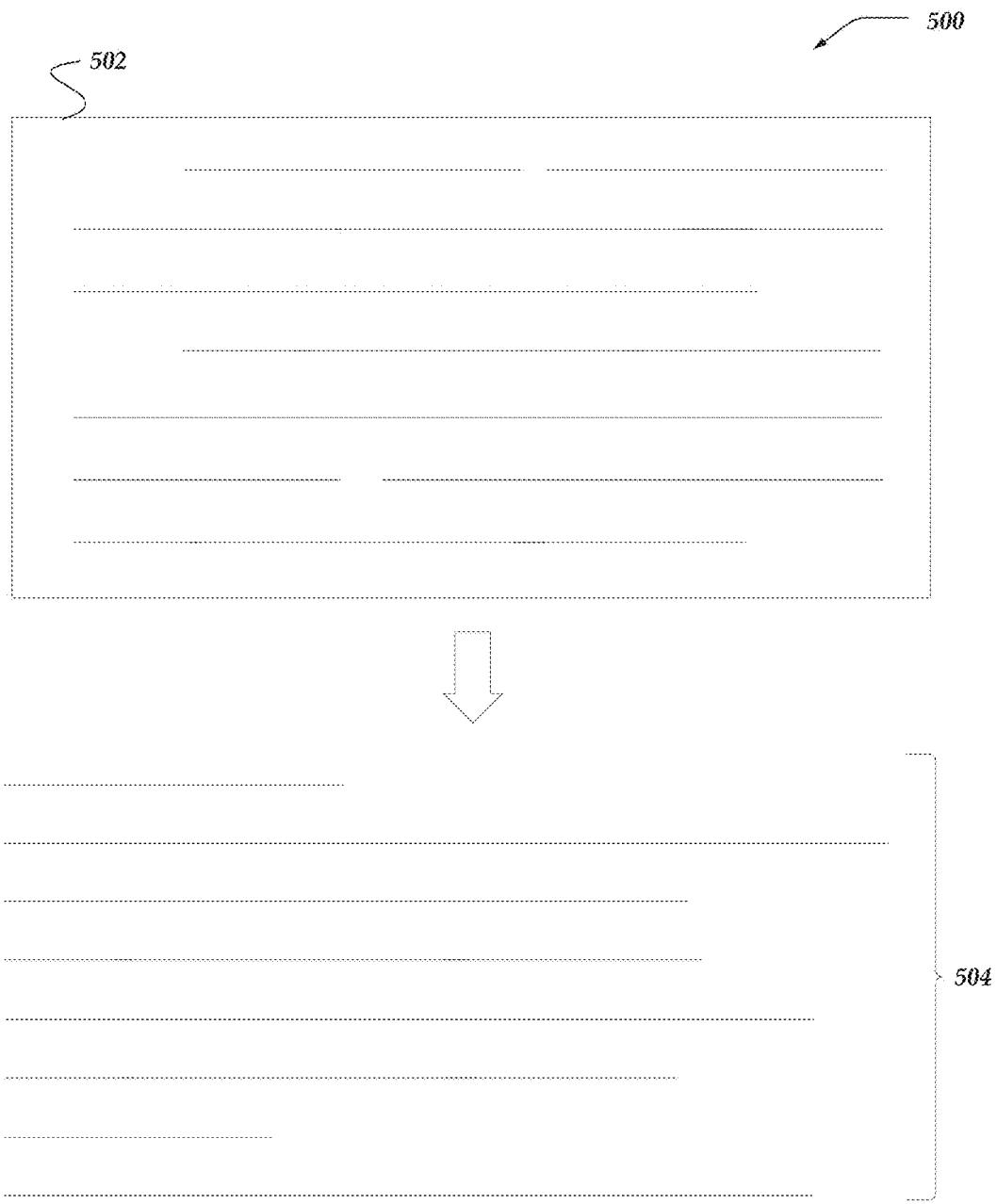
FIG. 5 illustrates one exemplary embodiment of sentence tokenization, in accordance with at least one of the various embodiments.

FIG. 5 illustrates one exemplary embodiment 500 of a first step in comment analysis—sentence tokenization. In one or more of the various embodiments, reviewers may generate one or more paragraphs of text. Additionally or alternatively, reviewers may dictate text which is later may be transcribed or in real-time converted into text via speech to text technology.

In either case, one embodiment of the claimed embodiments tokenizes (splits) the text into sentences. Sentences may be tokenized based on punctuation, sentence structure, a grammatical analysis, or the like. For example, FIG. 5 depicts comment 502 being tokenized into sentences 504. However, other embodiments of the claimed embodiments are similarly contemplated. For example, commentary may be tokenized by phrase, by line, or not tokenized at all.

Figure 6:
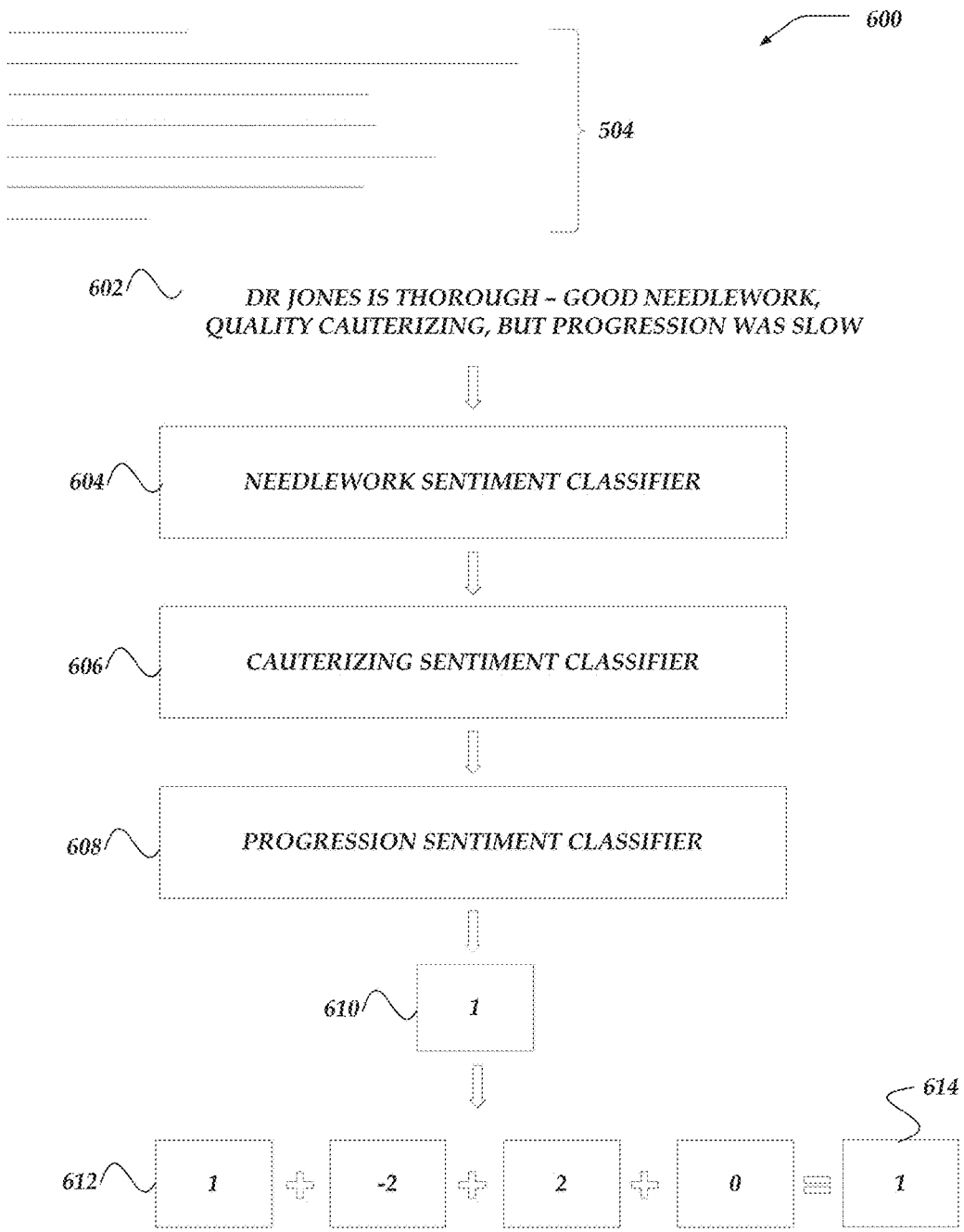
FIG. 6 illustrates one or more of the various embodiments of commentary classification performed in one embodiment by ATSC 110.

FIG. 6 illustrates one or more of the various embodiments 600 of commentary classification performed in one embodiment by ATSC 110. Commentary classification may be performed by passing input, in this case sentence 602, through one or more classifiers, such as needlework sentiment classifier 604, cauterizing sentiment classifier 606, and progression sentiment classifier 608. These classifiers are merely examples, and any other types or numbers of classifiers are similarly contemplated. In one embodiment, classifiers 604-608 have been trained with multiple examples of "ground truth" identifying examples of positive, negative, and neutral sentiment for their respected input, as identified by human trainers. For example, needlework or suturing sentiment classifier 604 may be a neural network trained by being supplied with many examples of sentences which describe suturing, along with a ground truth indication of positive, negative, or neutral sentiment. From this input data the neural net internally, without human intervention, identifies patterns, rules, and heuristics to properly classify novel sentences.

Each classifier examines, in this example, sentence 602 ("Dr. Jones is thorough—good needlework, quality cauterizing, but progression was slow") and determines if the sentence contains content satisfying the classification. For example, needlework sentiment classifier 604 may have been trained to recognize both "good needlework" and "quality suturing" as positive sentiment. Similarly, cauterizing sentiment classifier 606 may have been trained to recognize "quality cauterizing" as positive sentiment. However, progression sentiment classifier may have been trained to recognize "slow progression", and so assigned "but progression was slow" a negative sentiment. In one embodiment, a numeric value of "1" is given to every instance of positive sentiment, and "−1" to every instance of negative sentiment.

Other sentiment classifiers may be trained to recognize "scraping", "smoke", "bleeding", "favors right hand", "moves really slowly through the surgery" and the like as negative sentiment. Classifiers may be also be trained to recognize "good bimanual dexterity", "excellent depth perception", "quick progression", "solid pull of the needle", and the like as having positive sentiment.

In one embodiment, different classifiers are used for different types of commentators. For example, surgical colleagues may have their commentary processed by a classifier that has been trained with technical surgical language such as "suturing", while assistants or lay people may have their commentary processed by a classifier that has been trained with less formal language, such as "stitches". In one embodiment, a correlation between comments made by subject matter experts and lay individuals is performed so that comments from all types of reviewers can be aggregated.

Following the application of each classifier, in one or more of the various embodiments, sentiment from each classifier is added together to determine a sentiment for the sentence. Continuing the example, 2 positive and 1 negative sentiments are added to give a sentiment 610 of "1" to sentence 602.

In one or more of the various embodiments, multiple sentences have their sentiments aggregated to generate an overall sentiment of a paragraph or a complete commentary. For example, sentiments 612 of 1, −2, 2, and 0 are summed to determine a sentiment 614 of "1" for an entire paragraph/commentary.

Figure 7:
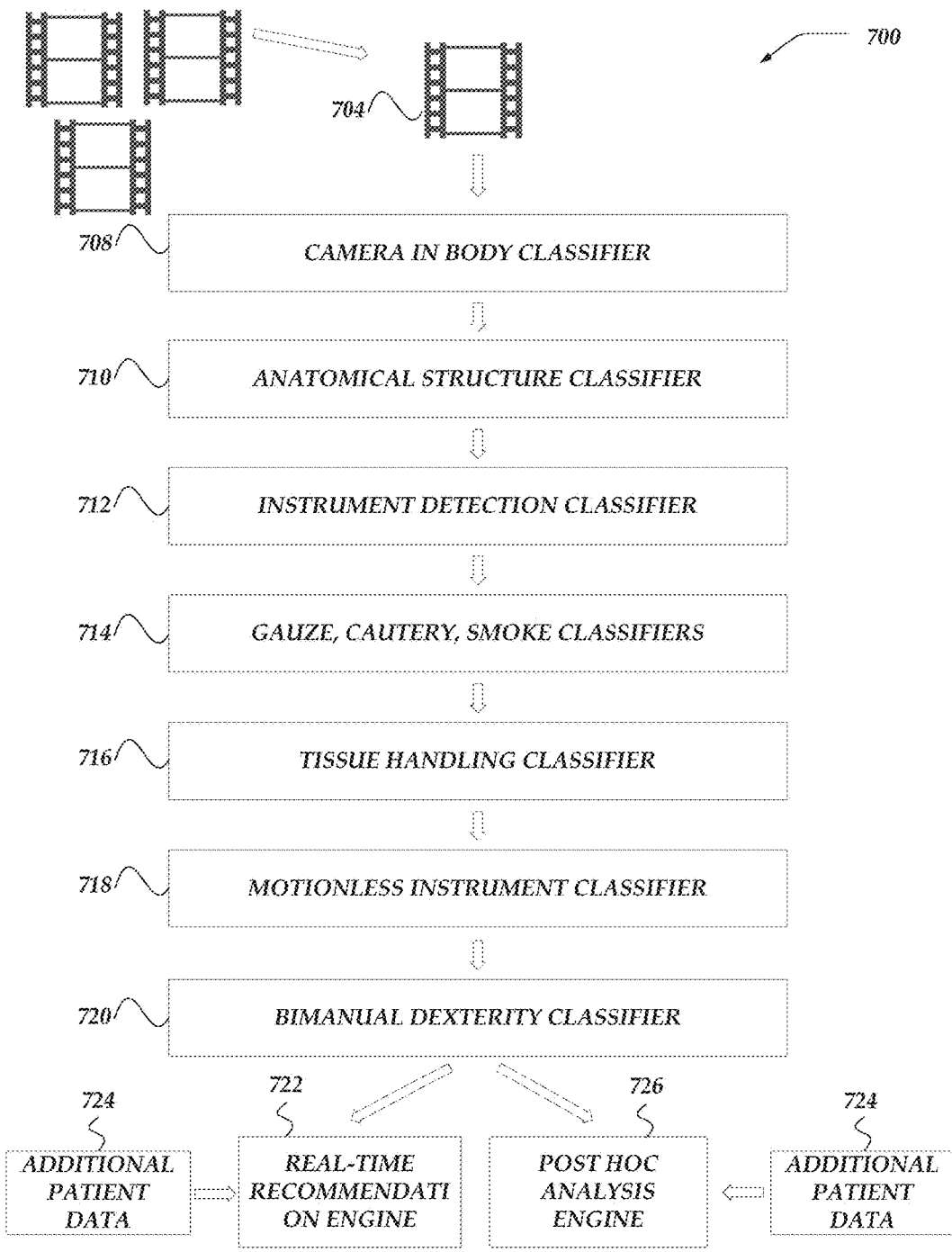
FIG. 7 illustrates one or more of the various embodiments of video classification performed in one embodiment by ATSC 110.

FIG. 7 illustrates one or more of the various embodiments 700 of performance content classification such as video classification performed in one embodiment by ATSC 110. Video classification may be performed by passing a video clip, such as video clip 704, through one or more classifiers, such as camera in body classifier 708, anatomical structure classifier 710, instrument detection classifier 712, gauze, cautery, and smoke classifiers 714, tissue handling classifier 716, motionless instrument classifier 718, and bimanual dexterity classifier 720. These classifiers are merely examples, and any other types or numbers of classifiers are similarly contemplated. Each classifier is trained with a ground truth—i.e. a set of videos identified by a human expert to contain (or not contain) the question at issue. As a video clip is processed by each classifier, indications of and/or a degree to which the classifier determines that the video clip contains the indicated activity are identified.

In one or more of the various embodiments, video clips may be cached locally on the video cameras, video capture systems, a local capture agent or local network computer. Accordingly, in one or more of the various embodiments, the local capture agent may be arranged to monitor network quality or connectivity. In some embodiments, the local capture agent may be arranged to store performance content, such as video clips, locally and then upload to a data store for processing. In one or more of the various embodiments, the local capture agent may be arranged to apply one or more rule-based policies than are applied to determine when or if performance content should be uploaded. Also, in some embodiments, the rule based policies may be include instructions or configuration information that may be compiled or interpreted into machine instructions that may be executed by the capture agent. In some embodiments, the rule based policies may policies that relying on one or more monitored metrics, such as, network bandwidth, network utilization, latency, costs, or the like. For example, in some embodiments, a rule may be provided that limits or restricts performance content uploads to those times where a hospitals network is less utilized. Likewise, in some embodiments, some performance content may be tagged as having different policy (e.g., QOS considerations) than other performance content. For example, high priority performance content may uploaded before lower priority content.

In some embodiments, the capture agent may be arranged to automatically begin caching if network connectivity is lost. Thus, the performance may continue unabated without the loss of the performance content. Accordingly, in some embodiments, in this example, if the network comes back online the cached performance content may be uploaded as per defined policies.

Additionally, in one or more embodiments, the performance content may be processed at least in part remotely to conserve local resources that are employed in real time to process the performance content. In one or more embodiments, all of the raw performance content is not saved to conserve both local and remote storage resources. For example, classifications, correlation values, reports, recommendations, metadata, and those portions of the performance content that correspond to particular surgical steps may be stored persistently rather than storing the entirety of the performance content.

Further, in some embodiments, localization services based on GPS signals or Wi-Fi network signals may be used to transform date stamps, time stamps, units, metadata or the like, to match the either the source of the performance content or the destination of the content. In some embodiments, information localized to the locale where the performance content is captured may be generated and sent along with the performance content. Accordingly, in one or more of the various embodiments, assessment engines or other third party services may make use of the localized information to provide additional context regarding the performance content. For example, the additional context may include metadata that optimizes the performance content for users based on one or more of linguistics, cultural preferences, geographic regional preferences, political preferences, religious preferences, holidays, weather information, disaster information, technical parameters, time zones, configuration parameters, units of measurement, monetary units, or the like. Also, in one or more of the various embodiments, machine learning used for generating classifiers may be arranged to consider this additional context as part of their analysis.

In one embodiment, camera in body classifier 708 determines whether a camera, such as endoscopic camera 118, is inside the body or not. This is a threshold determination before performing additional processing, and may serve as the basis for a warning should a camera designed to be within the body should fall out. Determining whether a camera is in a body is not trivial, as the lens may become pressed against the inside of the person and/or covered in fluid, obscuring the lens.

In one embodiment, anatomical structure classifier 710 determines and/or outlines when one or more anatomical structures are visible. For example, anatomical structure classifier may identify and distinguish veins, arteries, nerves, muscle, bone, ligament, adipose tissue, or other important and/or sensitive body parts. Identification of these items may be used, alone or in conjunction with other classifiers. For example, anatomical structure classifier may be used in conjunction with instrument detection classifier 712 to warn a subject of a risky or impending mistake, when the surgeon is performing the activity at a location that is unsafe, wrong location, or out of bounds in the patient, or when the surgeon is taking too long to perform the activity, and then to provide a personalized recommendation back to the performing surgeon for real time decision support and/or post performance as a prescriptive improvement opportunity to be applied to future cases.

In one embodiment, instrument detection classifier 712 identifies and/or outlines instruments in use during the procedure. As discussed above, this information can be used with other classifiers to provide recommendations, gather statistics on a particular subject or for a particular step, or the like. Furthermore, results from instrument detection classifier 712 may be used in conjunction with knowledge of what step the subject is about to attempt, possibly in conjunction with a cost estimate and outcome prediction of continuing to use the current instrument. In one embodiment, these factors are weighed and a recommendation of a new instrument is recommended. For example, a subject may be advised to switch the vessel sealer for monopolar shears, because it only takes 3 minutes to switch, and time is saved by using the different tool. Additionally, a size of the current instrument and the hand size and handedness of the subject is compared to various factors, including a size of the patient, to identify a potential mismatch, such as a size or an orientation of the current instrument, that could create negatively impact the performance of the activity.

In one embodiment, gauze, cautery, and smoke classifiers 714 identify events, both expected and unexpected, during a surgical activity. For example, in conjunction with knowledge of the surgical activity, output from gauze and cautery classifiers 714 may be used to confirm that gauze and cautery are being used as expected. Furthermore, output from smoke classifier 714, including a degree of smoke detected, may be used to identify when cautery has been over used or is taking too long to perform.

In one embodiment, tissue handling classifier 716 indicates when tissue has been positive or negative. In one embodiment, suturing is evaluated to determine if the pull was appropriately strong, if the tissue was approximated well, that the sutures were neither too tight nor too loose, etc. Similarly, tissue handling classifier 716 may indicate when cauterization is sufficient to keep the surgical field free of excess blood. The output of tissue handling classifier 716 may be directed in real-time to a subject, particularly when a negative outcome has been observed. In another embodiment, the output of tissue handling classifier 716 may be stored in metadata 120 for subsequent mining and analysis.

In one embodiment, motionless instrument classifier 718 indicates whether an instrument in the patient's body has become motionless. Typically this indicates a mistake or oversight, including but not limited to the loss of a surgical tool inside the patient.

In one embodiment, bimanual dexterity classifier 720 evaluates the bimanual dexterity of the subject—i.e. it evaluates whether the subject uses both hands well, or whether she favors one hand or another. Output from this classifier may be stored in metadata 120 for subsequent mining and analysis. For example, subject with better or worse bimanual dexterity may tend to perform better or worse at certain steps or certain surgical activities. These data are then provided back to the subject as personalized recommendations for real time decision support during performance and/or post performance as a prescriptive improvement opportunity to be applied to future cases.

Upon completion of the classifiers, the video clips and the results of the classifiers may be processed by real-time recommendation engine 722, post hoc analysis engine 726, or both. Real-time recommendation engine 722 may, with the optional input of additional patient data 724, produce real time recommendations to subject surgeon 402. These recommendations may be displayed on monitor 416 or augmented reality glasses 418. For example, when the subject/surgeon is performing the activity too slowly, when the surgeon is performing the activity in a location that is unsafe, the real-time recommendation engine 722 can provide various recommendations to improve the outcome of the surgery activity. The recommendations may include a different technique to perform the surgery, a different instrument to perform a surgical step, a medication or treatment to be administered to the patient, or notify another surgeon with positive results previously performing this surgery activity that the current surgeon is likely to need assistance. The notification can include one or more of a message, email, telephone communication, and/or link to a real time video of the surgery. Post hoc analysis engine 726, with the optional input of additional patient data 724, may identify positive and negative portions of the surgery, including a list of improvements to make.

In one embodiment, additional patient data 724 may include attributes describing the patient's demographics, the patient's health, the patient's surgical history, the patient's disease state, or any other relevant information. This information may be used to augment the results of the classifiers, such as, for example, refining the result of anatomical structure classifier 710 (or choosing from a different anatomical structure classifier) based on the age, gender or medical history of the patient.

As discussed above, in one or more of the various embodiments, classifiers 708-720 are trained by being supplied with a corpus of sample data, thereby establishing ground truth. For example, camera in body classifier 708 may be a neural network trained by being supplied with many examples of videos marked by humans to include a camera in the body, as well as examples of videos marked by humans to include a camera out of the body. However, certain classifiers may be trained with data extracted from commentary, as discussed above in conjunction with FIG. 6. For example, if commentary generated by experts for a portion of a surgical activity indicates excellent tissue handling, the corresponding video and ground truth may be used as input to tissue handling classifier 716.

Figure 8:
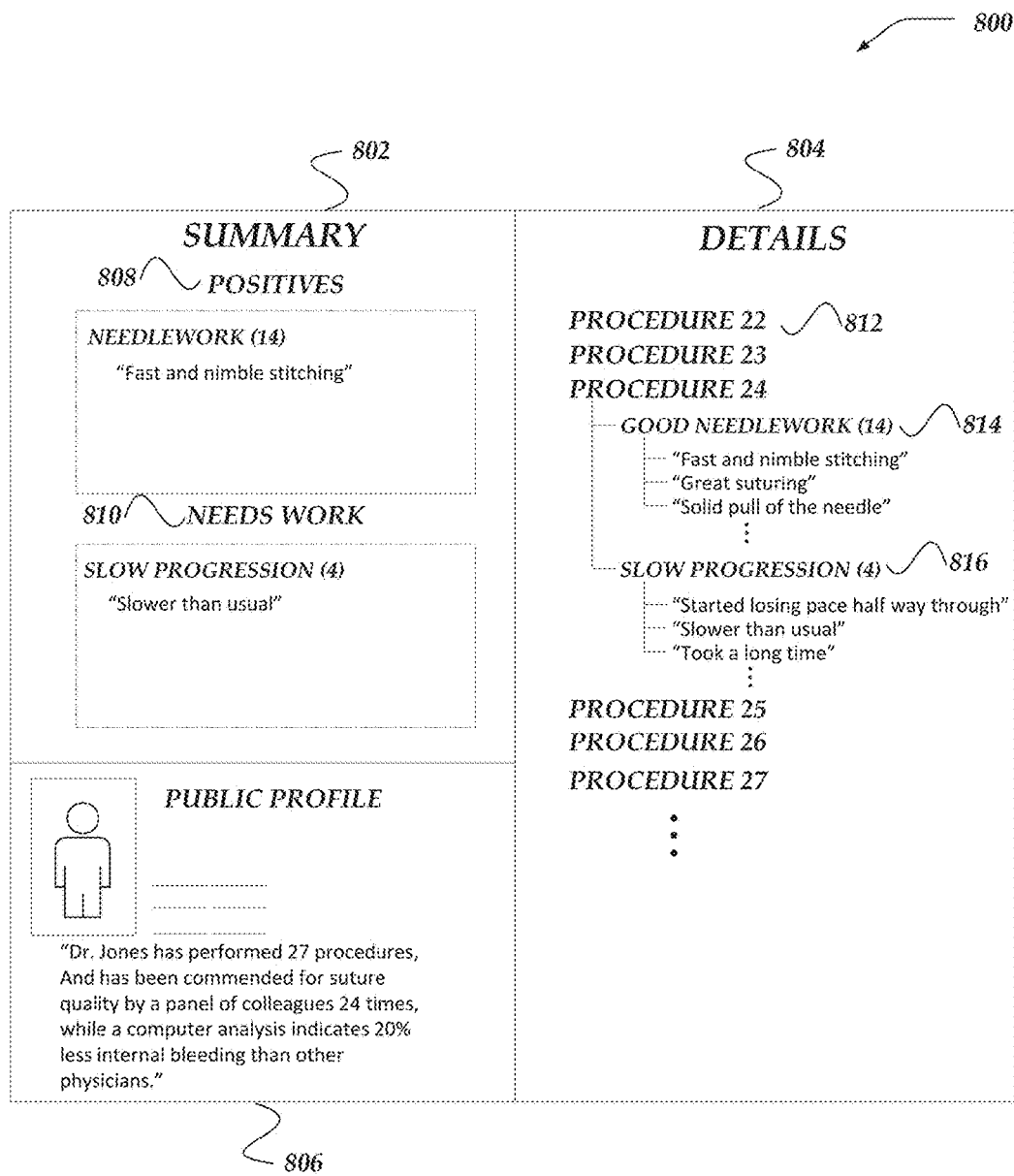
FIG. 8 illustrates a profile page viewable in an "App" or web-browser, in accordance with at least one of the various embodiments.

FIG. 8 illustrates a profile page 800 viewable in an "App" or web-browser. The profile page may include a summary portion 802, a details portion 804, and/or a public profile portion 806.

In one or more of the various embodiments, the summary portion 802 contains one or more summaries of a subject's performance. The summary may include skills 808 that are "positives"—i.e. skills the subject performs well, and skills 810 that "needs work"—i.e. skills that the individual performs poorly. In one embodiment, skills are identified as positive or negative based on classifiers and optional additional processing applied to commentary and/or video streams, as discussed below with regard to FIGS. 9 and 10, respectively. In one or more of the various embodiments, each entry in the summary is identified by a representative comment, e.g. "Fast and nimble stitching" and "Slower than usual".

In one or more of the various embodiments, the subject's strengths and weaknesses may be reported or shown relative to other similar subjects like them across a data set procedure assessments. For example, "You surgeries are 25% more likely to involve rough tissue handling, which is expected to result in 20% higher complications than your peers." Then, those observations may be turned into personalized recommendations for improvement that are statistically most likely to produce the skill improvement and patient outcomes they desire.

In one or more of the various embodiments, the details portion 804 may include a list of procedures 812 performed by the subject, each element of which can be expanded to view detailed aggregated feedback extracted from commentaries. For example, procedure 24 has been expanded, and two activities are listed as significant (i.e. appeared above a threshold percentage of commentaries)—"good needlework" 814 and "slow progression" 816. Each of these activities may themselves be expanded to see the actual sentence fragments containing the description of the activities, such as "fast and nimble stitching" or "slower than usual".

In one or more of the various embodiments, a surgeon subject is enabled to flag a comment as wrong. In these instances, a trained reviewer will be assigned to review the video and flagged comment. If the surgeon subject is deemed correct, the comment is removed. If the commentator is deemed cored, then the correct classification is added as ground truth available for subsequent classifier training.

In one or more of the various embodiments, the public profile 806 indicates what users of a social network may see upon visiting the subject's profile page. In one embodiment the content of the public profile is computer generated based on the results of commentary and/or video classification, as discussed herein. In this way, viewers of the public profile can have confidence in the accuracy and impartiality of the data contained therein. The social network may be purpose built to include such profiles, or the content may be integrated into existing social networks.

Generalized Operations

The operation of certain aspects of the invention will now be described with respect to FIGS. 9-11. In at least one of various embodiments, processes 900, 1000, and 1100 described in conjunction with FIGS. 9-11, respectively, or portions of these processes may be implemented by and/or executed on a network computer, such as network computer 300 of FIG. 3. In other embodiments, these processes or portions of these processes may be implemented by and/or executed on a plurality of network computers, such as network computer 300 of FIG. 3. Also, in at least one of the various embodiments, these processes or portions of these processes may be implemented by and/or executed on one or more cloud instances operating in one or more cloud networks. However, embodiments are not so limited and various combinations of network computers, client computer, cloud computer, or the like, may be utilized. These processes or portions of these processes may be implemented on any computer of FIG. 1, including, but not limited to documenting computers 112-118, reviewing computers 102-107, or ATSC 110.

Figure 9:
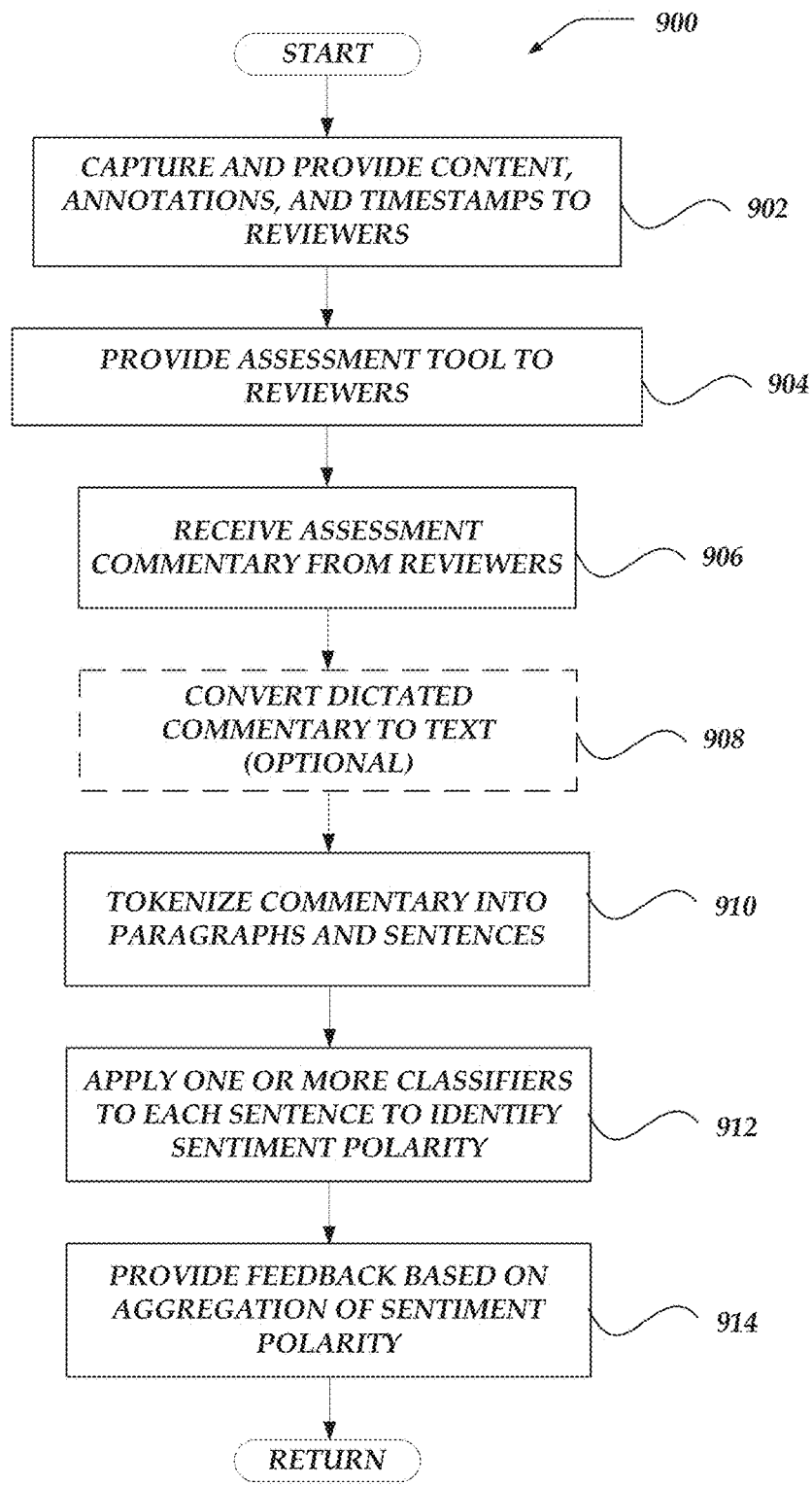
FIG. 9 shows an overview flowchart for a process to provide feedback based on an aggregation of sentiment polarity extracted from commentary received by reviewers.

FIG. 9 shows an overview flowchart for process 900 to provide feedback based on an aggregation of sentiment polarity extracted from commentary received by reviewers. After a start block, at block 902, in at least one of the various embodiments, content documenting the subject procedure is captured. In one or more of the various embodiments, content that documents the performance of subject activity is captured via a content capturing device, such as but not limited to a documenting computer. For instance, at least one of the documenting computers 112-118 of FIG. 1 may capture content documenting subject activity performed by a subject.

The captured content may be any content that documents the subject activity, including but not limited to still images, video content, audio content, textual content, biometrics, and the like. For example, a video that documents a surgeon performing a surgery (including but not limited to a robotic surgery) may be captured. In other embodiments, a video of a phlebotomist drawing blood from a patient or a video of a nurse operating a glucometer to obtain a patient's glucose level may be captured. The content may document the subject performing various protocols, such as a handwashing protocol, a home dialysis protocol, a training protocol, or the like. As discussed further below, at least a portion of the captured content is provided to reviewers, such as colleagues, mentors, or other subject matter experts. As discussed throughout, the reviewers review the content and provide commentary, text based or dictated, in regards to the performance of the subject activity. Each reviewer provides commentary that indicates their independent assessment of the subject's performance of the subject activity.

In one or more of the various embodiments, the subject, an operator of documenting computers 112-118, or another person with knowledge of the activity may generate annotation suggestions in real-time. Additionally or alternatively, one or more of these people may create timestamps with markers as significant events occur. Additionally or alternatively, one or more of these people may tag significant events as occurring, enabling a reviewer to "fast forward" to particular events, filter based on certain event types, and the like.

At block 904, an assessment tool is associated with the content captured at block 902. In one embodiment the assessment tool solicits a text-based or dictated commentary from a reviewer. The commentary may be in response to an open-ended qualitative question, or in response to a prompt for generalized comments, feedback, and the like.

In one or more of the various embodiments, metadata, such as a timestamp, may be overlaid on the content by the assessment tool. In another embodiment, audio captured concurrently from one or more sources may be played back with the video content, enabling the reviewer to understand what one or more people performing the activity were saying at the time. In another embodiment, features extracted from the video by a machine learning system may be highlighted or otherwise identified, such as the location of anatomical features, the location of surgical instruments, or the like, as discussed below in conjunction with FIG. 10.

In various embodiments, a reviewer may be a user of a reviewing computer, such as, but not limited to reviewing computers 102-118 of FIG. 1. In at least one embodiment, the content is provided to a reviewer via a web interface. For instance, a link, such as a hyperlink, may be provided to a reviewer that links to the web interface.

At block 906, assessment commentary is received from reviewers. In one embodiment the assessment includes a text-based assessment typed by the reviewer. However, a dictated assessment is also contemplated, which may be transcribed for further processing.

In one embodiment, metadata associated with the commentary is also received with the commentary. In one embodiment, the time at which portions of the assessment were made relative to playback of the content is included in the metadata. For example, if a portion of the commentary was generated 23 minutes into a procedure, an indication as such would be included in the commentary. In this way, if during a surgical procedure, cauterization was performed at 6, 23, and 50 minutes into the procedure, a correlation between the comment and the actual event could be established. For example, if the comment referenced cauterization, it could be determined with a high level of confidence that the comment referred to the cauterization that occurred at the $23^{rd}$ minute.

At block 908, optionally, dictated commentary is converted to text. However, in another embodiment, dictated commentary is processed by audio classifiers to extract features similar to the features extracted from text based commentary, as discussed below.

At block 910, in one or more of the various embodiments, the commentary is tokenized into paragraphs and sentences. Paragraphs may be identified in one embodiment by tabs and newline characters, while sentences may be tokenized based on an analysis of sentence structure, grammar, and punctuation.

At block 912, one or more classifiers are applied to each of the sentences, as discussed above in conjunction with FIG. 6.

At block 914, feedback is provided based on the aggregation of sentiment polarity identified in block 912. In one embodiment, the feedback is depicted in a subject's profile, discussed above in conjunction with FIG. 8. Similarly, feedback may be aggregated and summarized in a "summary" and "details" page as discussed above in conjunction with FIG. 8.

In one embodiment, feedback based on aggregation of sentiment polarity may be used to train a machine learning system, discussed below in conjunction with FIG. 10. For example, an example of excellent suturing, as determined by a significant percentage (e.g. above 90%) of reviewers remarking positively about a particular step, may be provided to a machine learning system as training material for identifying excellent suturing. In other embodiments, the three best scores for a particular step may be recommended as a learning opportunity for the machine learning system.

In another embodiment, particularly positive or negatively reviewed portions of an activity may be identified as a personalized, prescriptive learning opportunity for the subject or other practitioners. As such, superior and deficient content may be provided, e.g. via a profile page, so that a viewer of a report may compare and contrast superior examples with deficient examples.

An another of the various embodiments, feedback is provided as real-time advice to the surgery subject, appearing on screen 416 or glasses 418 worn by the subject 402.

Process 900 then passes to a return block.

Figure 10:
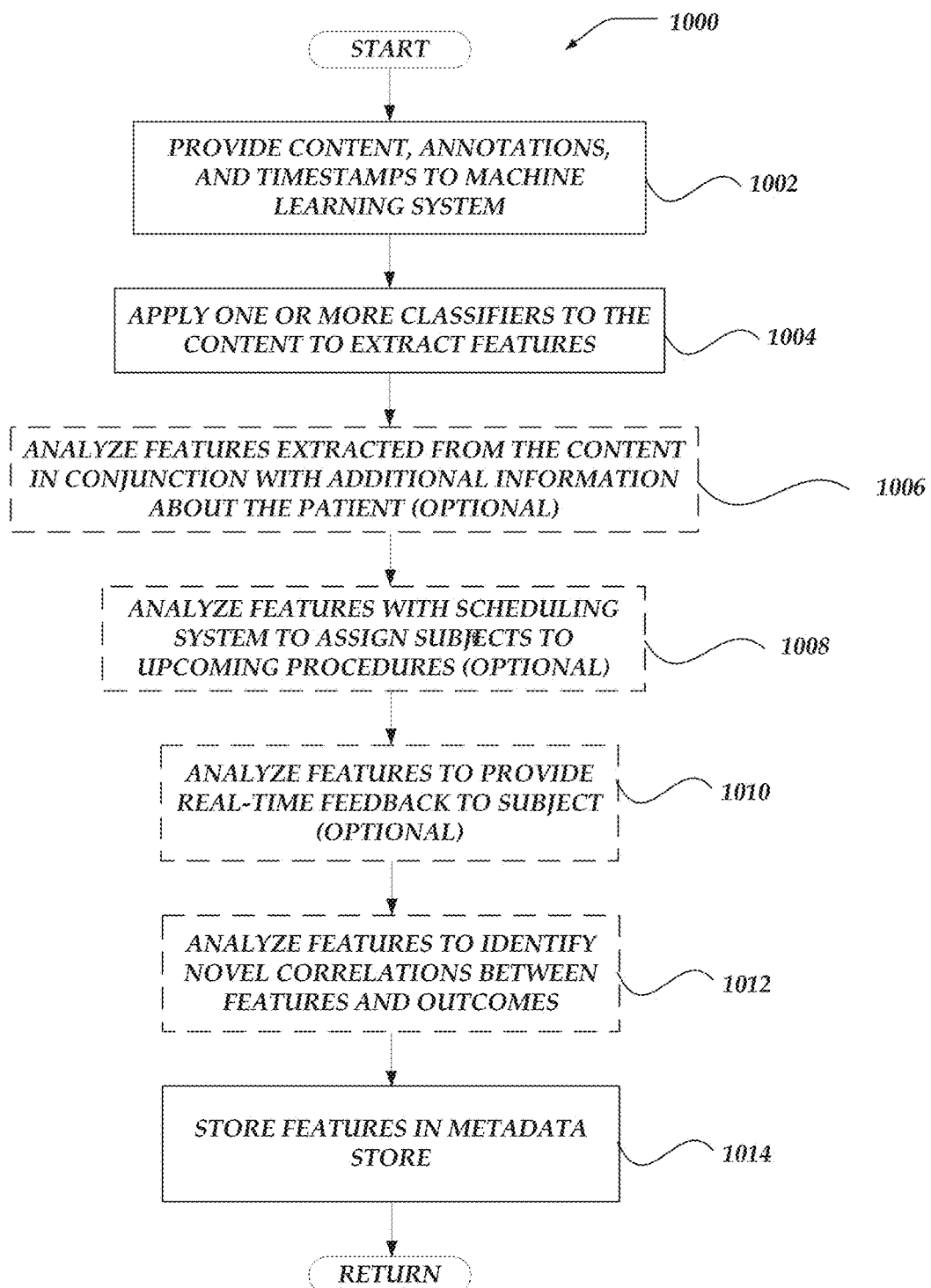
FIG. 10 shows an overview flowchart for a process for applying a machine learning system to analyze video of an activity.

FIG. 10 shows an overview flowchart for process 1000 for applying a machine learning system to analyze video of an activity. In one embodiment, the content processed by process 1000 is similar to the content processed by process 900. The processing may similarly occur in real time, enabling real time feedback. Additionally or alternatively, the processing may be applied to archival footage of an activity, in which case results are used to predict performance and patient outcomes of future cases performed by the subject, provide personalized feedback and prescriptive recommendations for improvement activities to the subject, identify training materials, provide rankings usable to schedule subjects for upcoming activities, and the like.

After a start block, at block 1002, content, annotations, and timestamps are provided to a machine learning system for analysis. In one or more of the various embodiments, content that documents the performance of subject procedure is captured via a content capturing device, such as but not limited to a documenting computer. For instance, at least one of the documenting computers 112-118 of FIG. 1 may capture content documenting subject procedure performed by a subject. In general, the content is captured as discussed above in conjunction with block 902 of FIG. 9.

At block 1004, one or more classifiers are applied to the content, as discussed above in conjunction with FIG. 7.

At block 1006, optionally, features extracted from the content are analyzed in conjunction with additional information about the patient. For example, if it is known that the patient has a virulent form of cancer, it may be decided that additional risks are worth taking during this procedure. As a result, features indicating a risky step, e.g. a scalpel passing too close to an artery, may be downgraded or ignored for purposes of real-time feedback.

At block 1008, optionally, a scheduling system is employed to use features extracted from the content to assign subject to upcoming activities. For example, if a surgeon exhibits slow progression during a procedure, this information may be used by an administrative scheduling system to avoid assigning the surgeon to complex cases that require faster movements. Similarly, if a surgeon exhibits particular skill at one aspect of surgery, she may be assigned to subsequent cases that require a disproportionate amount of that skill.

At block 1010, optionally, features are analyzed to provide real-time feedback to the subject. In one embodiment, this feedback is provided on video monitor 416, while in another embodiment it is provided via heads up display glasses 418. For example, if one feature identifies the location of a surgical instrument, such as scalpel 414, and another identifies the location of a vulnerable anatomical structure, such as a ureter, block 1010 may provide a warning to the subject surgeon of the proximity of the scalpel to the ureter, and suggest backing off.

At block 1012, optionally, features are analyzed to identify novel correlations between features and outcomes. For example, knowledge originating from humans may not include subtle or complicates correlations identifiable by machine learning. For example, bi-manual dexterity may be more or less important in performing certain surgical techniques for certain types of surgery. Similarly, handedness, hand size, and other factors may be identified as leading to better or worse surgical outcomes.

Further, in some embodiments, additional outcome related insights may be discovered. For example, assessments or outcomes may be mapped to time of day, type of patient, type of procedure, or to other features associated with one or more of subjects, patients, assessments, or the like. Likewise, in some embodiments, outcome information may be generated based on a comparison of evaluation of procedures performed by other subjects, performed at other institutions, performed using the same or different instruments, or the like.

At block 1014, features extracted by the machine learning system are stored in metadata store 120.

Process 1000 then passes to a return block.

Figure 11:
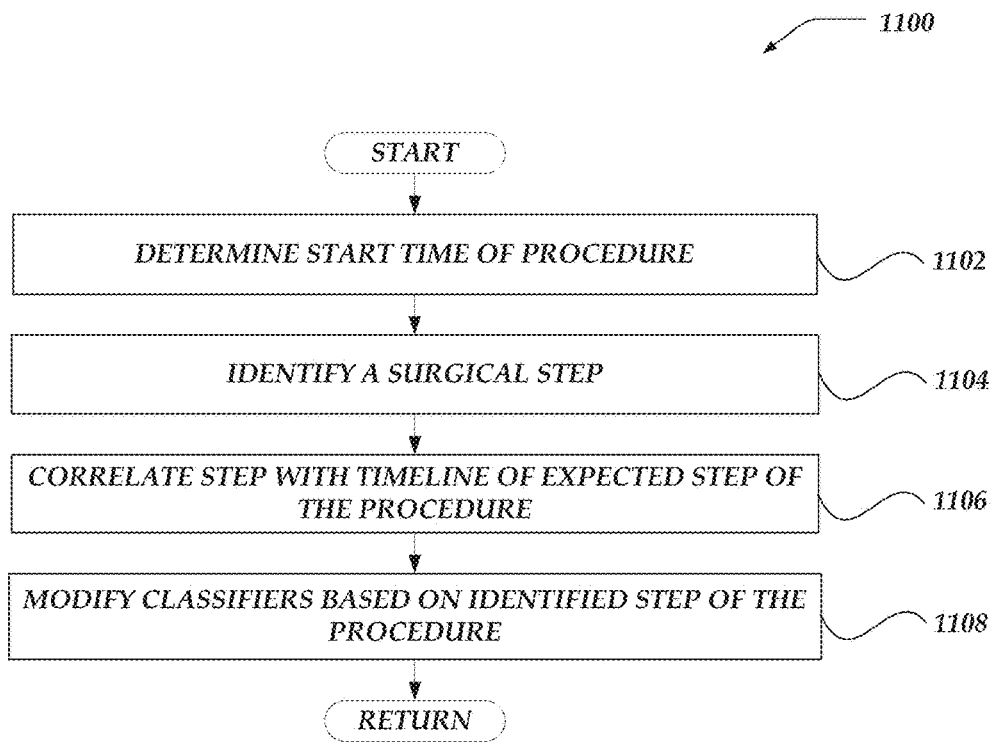
FIG. 11 shows an overview flowchart for a process for correlating an identified step with a timeline of expected steps for the activity being performed.

FIG. 11 shows an overview flowchart for process 1100 for correlating an identified surgical step with a timeline of expected surgical steps for the activity being performed. In one embodiment, process 1100 is executed in conjunction with FIG. 10, e.g. block 1004 of FIG. 10.

After a start block, at block 1102, the start time of a procedure is determined. In one embodiment the start time of the procedure is 00:00, although video clips of sub-portions of the activity may start at arbitrary times.

At block 1104, a surgical step is identified. In one embodiment the identified step includes a basic surgical step, such as an incision, suture, cautery, or the like. The step may be identified relative to a body part. Additionally or alternatively, the surgical step identified may be more complex, such as an excision of a particular anatomical structure (e.g. removal of an appendix).

At block 1106, a correlation between the identified step and a step expected to take place for the given activity is made. For example, an incision expected to occur around the 5$^{th}$ minute of an activity may be correlated with an incision observed to have occurred 5 minutes and 30 seconds into the procedure.

At block 1108, classifiers are modified based on the identified step. In one embodiment, based on the correlation with the timeline, particular classifiers may be selected or emphasized as applied to related (e.g. adjacent) portions of the content. For example, if the timeline of the activity shows that application of a spreader occurs within 15 seconds of the incision expected to occur around the 5$^{th}$ minute, classifiers that identify a spreader step, and/or evaluate aspects of a spreader step, are selected and/or emphasized around 5 minutes and 45 seconds into the content (i.e. 15 seconds after the actual incision was made).

Process 1100 then passes to a return block.

It will be understood that each block of the flowchart the illustrations, and combinations of blocks in the flowchart illustrations, can be implemented by computer program instructions. These program instructions may be provided to a processor to produce a machine, such that the instructions, which execute on the processor, create means for implementing the actions specified in the flowchart block or blocks. The computer program instructions may be executed by a processor to cause a series of operational steps to be performed by the processor to produce a computer-implemented process such that the instructions, which execute on the processor to provide steps for implementing the actions specified in the flowchart block or blocks. The computer program instructions may also cause at least some of the operational steps shown in the blocks of the flowcharts to be performed in parallel. Moreover, some of the steps may also be performed across more than one processor, such as might arise in a multi-processor computer system. In addition, one or more blocks or combinations of blocks in the flowchart illustration may also be performed concurrently with other blocks or combinations of blocks, or even in a different sequence than illustrated without departing from the scope or spirit of the invention.

Additionally, in one or more steps or blocks, may be implemented using embedded logic hardware, such as, an Application Specific Integrated Circuit (ASIC), Field Programmable Gate Array (FPGA), Programmable Array Logic (PAL), tensor processing unit (TPU), or the like, or combination thereof, instead of a computer program. The embedded logic hardware may directly execute embedded logic to perform actions some or all of the actions in the one or more steps or blocks. Also, in one or more embodiments (not shown in the figures), some or all of the actions of one or more of the steps or blocks may be performed by a hardware microcontroller instead of a CPU. In at least one embodiment, the microcontroller may directly execute its own embedded logic to perform actions and access its own internal memory and its own external Input and Output Interfaces (e.g., hardware pins and/or wireless transceivers) to perform actions, such as System On a Chip (SOC), or the like.

The above specification, examples, and data provide a complete description of the manufacture and use of the composition of the invention. Since many embodiments of the invention can be made without departing from the spirit and scope of the invention, the invention resides in the claims hereinafter appended.

Figure 12:
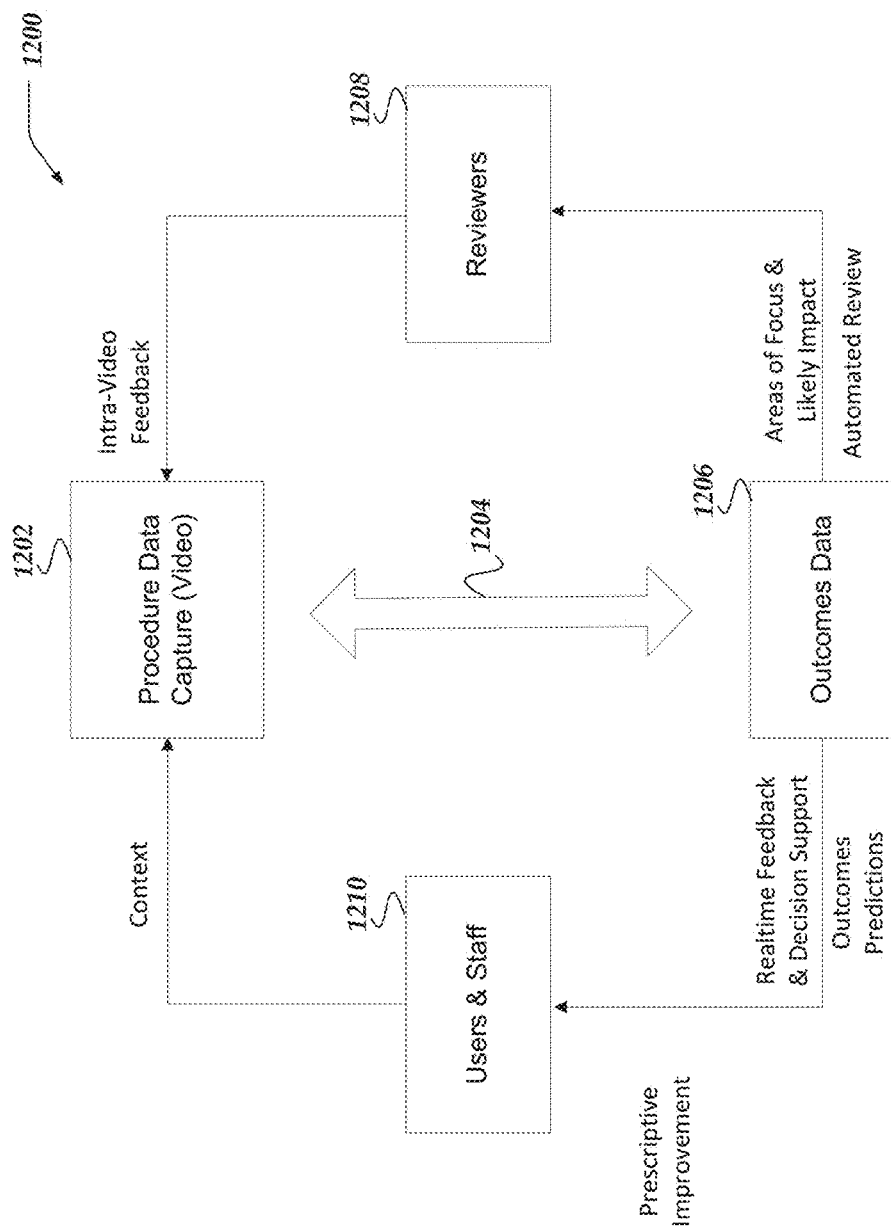
FIG. 12 illustrates a logical architecture of a system for automated assessment of operator performance in accordance with one or more of the various embodiments.

FIG. 12 illustrates a logical architecture of system 1200 for automated assessment of operator performance in accordance with one or more of the various embodiments. In one or more of the various embodiments, as discussed above, the performance of procedures may be captured using video camera, telemetry from instruments, or the like. In one or more of the various embodiments, captured procedure information may be communicated over various networks, such as, network path 1204, to various assessment tool computers that may analyze the captured procedure information and associated it with outcome data 1206. In one or more of the various embodiments, outcomes data 1206 may include information related to outcomes patients have had after undergoing procedures. Export reviewers, such as, reviewers 1208, may review performance content, such as, video presentations of the procedures. In one or more of the various embodiments, expert reviewers may review recorded video captured at the location of the procedure and then stored for later review. In some embodiments, expert reviewers may be enabled to do real-time reviews via streaming video, or the like. Accordingly, in some embodiments, expert reviewers may provide real-time corrections to operators performing the procedures. In other embodiments, the video being reviewed by expert reviewers may include one or more annotations included or generated based on an assessment engine, video classifiers, machine vision, or the like.

In one or more of the various embodiments, annotation information may include one or more points of emphasis based on evaluations or outcome information associated with performer of the procedure or other performers.

Further, in one or more of the various embodiments, user and staff 1210 represent the system users or performance support staff that may provide useful context information that may be associated with the procedure capture data. For example, users or staff may annotate performance data with context information, such as, highlighting point of interest, patient information, or the like. Also, in some embodiments, context information may include editing the procedure data to exclude activities that may be irrelevant to expert reviewers.

Figure 13:
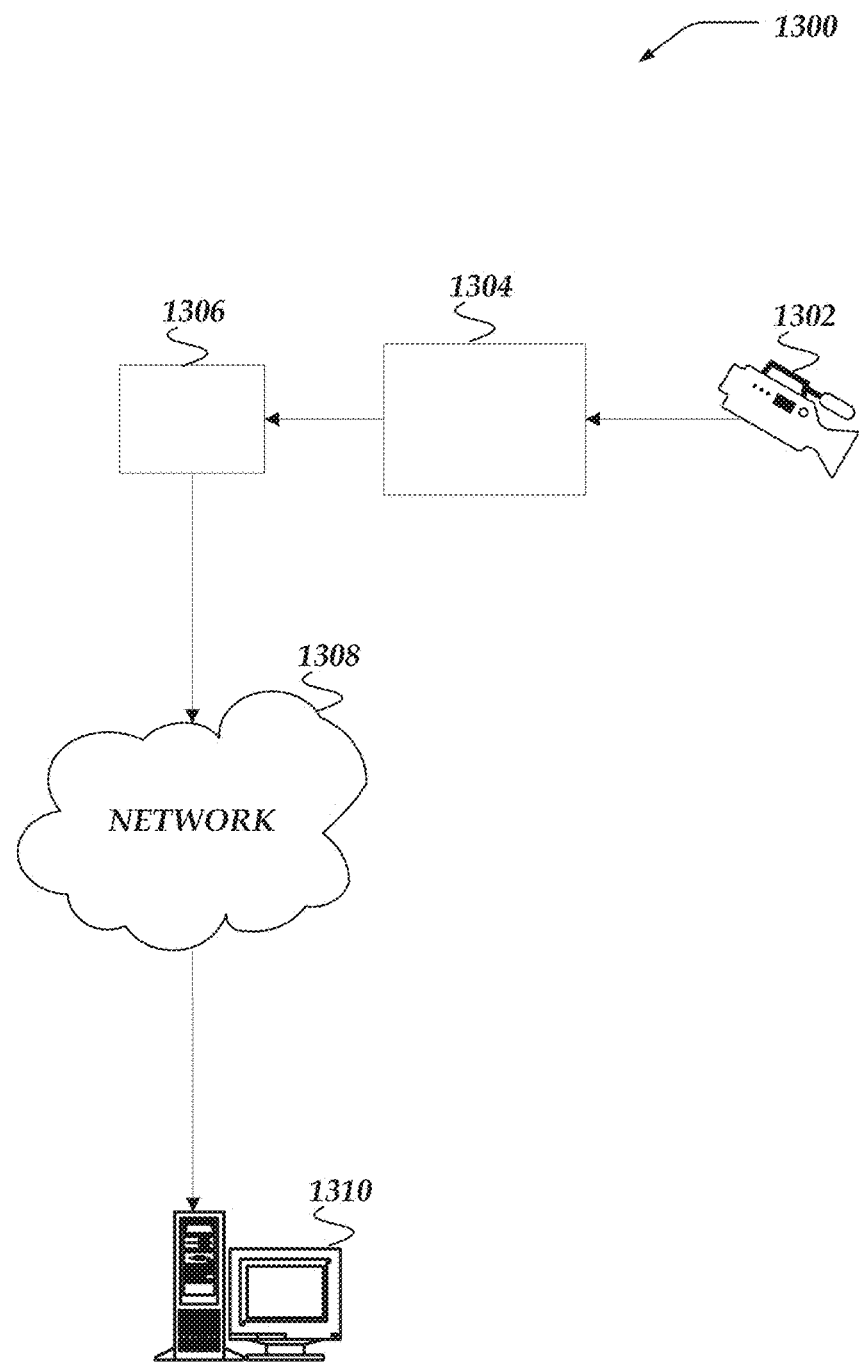
FIG. 13 illustrates a logical architecture of a system for automated assessment of operator performance that is in accordance with one or more of the various embodiments.

FIG. 13 illustrates a logical architecture of system 1300 for automated assessment of operator performance that is in accordance with one or more of the various embodiments. In one or more of the various embodiments, system 1300 includes one or more procedure data capture devices, such as camera 1302, a procedure instrument, such as, procedure instrument 1304, procedure capture client computer, 1306, network 1308, one or more assessment tool computers, such as, assessment tool computer 1310, or the like.

In one or more of the various embodiments, capture devices, such as capture device 1302 may include video cameras, ultrasonic scanners (e.g., tomographic reflection), audio microphones, optical position sensors, magnetic position sensors, or the like, or combination thereof. In some embodiments, one or more of the capture devices may be integral to procedure instrument 1304. Alternatively, in some embodiments, the capture devices may be external to the procedure instruments. In some embodiments, one or more capture devices may be connected to ports on the procedure instruments that provide data feeds to the capture device.

In one or more of the various embodiments, procedure instrument 1304 represents one or more instruments that may be part of the normal toolset (e.g., surgical systems) for performing the procedure. In some embodiments, procedure instrument 1304 may include advanced devices, that include integrated video capture, machine vision systems, heads-up displays, augment reality displays, one or more robotic arms, or the like, or combination thereof. In some embodiments, less advanced instruments may be used providing procedure data may be captured via one or more capture devices. For example, in some embodiments, video cameras may be arranged to capture surgical procedures performed using classic instruments, such as, stand-alone scalpels, suture needles, or the like.

In one or more of the various embodiments, procedure capture computers, such as procedure capture client computer 1306 may be coupled or otherwise integrated with one or more procedure instruments or one or more capture devices. In some embodiments, as described above, capture clients computers may be positioned at or close to where the procedure is being performed to capture procedure data. In some embodiments, procedure capture computers, such as procedure capture client computer 1306 may be integrated with a procedure instrument or procedure system rather than being physically separate from the procedure instrument.

In one or more of the various embodiments, network 1308 represents network that couples the procedure-side computer or devices to the assessment-side of the system. In one or more of the various embodiments, network 1308 may be considered to be similar or the same as network 108, or the like.

In one or more of the various embodiments, assessment tool computer 1310 may be considered to represent the one or more computers that provide support for storing, evaluating, classifying, or the like, captured procedure data. Likewise, assessment tool computer 1310 may be considered to represent one or more network computers that may host, instantiate or execute one or more of text classifiers 322, video classifiers 324, classification processing engine 326, and assessment engine 327, or the like.

One of ordinary skill in the art will appreciate that system 1300 illustrates one non-limiting example of a system that is in accordance with one or more of the various embodiments. Accordingly, other arrangements of computers, networks, devices, data capture devices, or the like, may be assembled to perform some or all of the innovation described herein. For brevity and clarity, these alternative arrangements are omitted. However, the examples and descriptions presented are at least sufficient to support the claimed subject matter.

Figure 14:
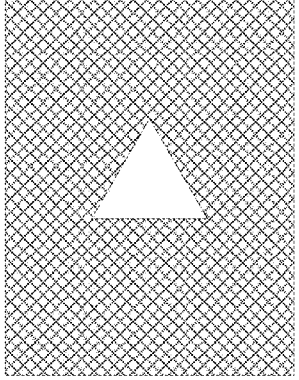
FIG. 14 illustrates a logical or functional representation of a user-interface for provided expert review information associated with a performed procedure in accordance with one or more of the various embodiments.

FIG. 14 illustrates a logical or functional representation of user-interface 1400 for provided expert review information associated with a performed procedure in accordance with one or more of the various embodiments. In one or more of the various embodiments, user-interface 1400 may include: one or more graphical user interface components, such as, window 1402; procedure data viewer 1404; one or more review/evaluation prompts with one or more accompanying input controls, such as prompt 1406 and control 1408, prompt 1410 and control 1412, prompt 1414 and control 1416, or the like; and, in this example, control 1418 may be a button for advancing to the next review action.

One of ordinary skill in the art will appreciate that user-interface 1400 illustrates one non-limiting example of a user-interface system that is in accordance with one or more of the various embodiments. Accordingly, other arrangements of user-interface elements may be assembled to perform some or all of the innovations described herein. For brevity and clarity, these alternative arrangements are omitted. However, the examples and descriptions presented are at least sufficient to support the claimed subject matter.

Figure 15:
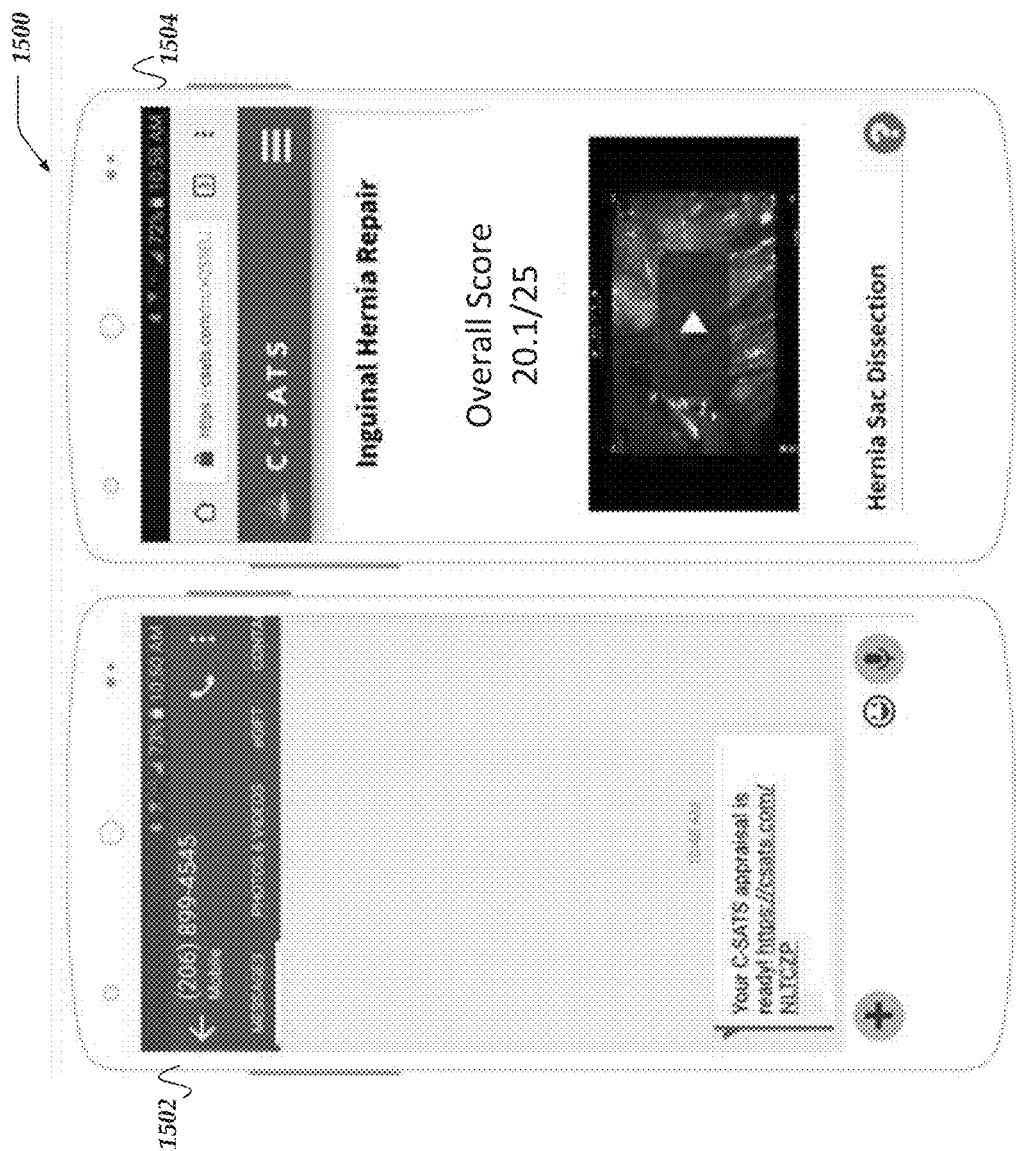
FIG. 15 illustrates a logical or functional representation of a user-interface for providing expert review information associated with a performed procedure in accordance with one or more of the various embodiments.

FIG. 15 illustrates a logical or functional representation of user-interface 1400 for providing expert review information associated with a performed procedure in accordance with one or more of the various embodiments. In this example, user-interface 1500 shows two screens from a mobile device interface or application (mobile phone app) for interacting with the assessment tools. In this example, screen 1502 shows a notification being provided to a subject (e.g., a surgeon) that indicates an assessment report is available. Accordingly, in one or more of the various embodiments, the subject may open the notification or otherwise instantiate an client assessment tool screen, such as screen 1504, that enables the subject to review or interact with the assessment report. Likewise, other views or screens may be provided as appropriate to enable subjects to read or interacts with their assessments. Also, in one or more of the various embodiments, mobile apps may be arranged to provide user, staff, expert reviewers, non-expert reviewers, administrators, or the like, access to various features of an assessment system.

One of ordinary skill in the art will appreciate that user-interface 1500 illustrates one non-limiting example of a user-interface system that is in accordance with one or more of the various embodiments. Accordingly, other arrangements of user-interface elements may be assembled to perform some or all of the innovations described herein. For brevity and clarity, these alternative arrangements are omitted. However, the examples and descriptions presented are at least sufficient to support the claimed subject matter.

FIG. 16 illustrates a logical or functional representation of data model 1600 for representing assessment scores for one or more portions or steps of assessed procedures in accordance with one or more of the various embodiments. In this example, various assessment features, such as depth perception, bimanual dexterity, efficiency, force sensitivity, robotic control, or the like, are associated with various binned or bucketed score values. The meaning of the different score may vary depending on the feature it may be associated with. Note, data model 1600 represents one way of representing score data associated with assessments. One of ordinary skill in that art will appreciate assessment systems in accordance with one or more of the various embodiments, may include more or fewer features, or the like. Also, in some embodiments, there may be more or fewer score buckets or score bins than shown here. However, data model 1600 is at least sufficient to enable one or ordinary skill that to practice the innovations described herein.

What is claimed as new and desired to be protected by Letters Patent of the United States is:

1. A method for assessing performances of physical activities wherein one or more processors in one or more network computers execute instructions to perform actions, comprising:
 employing one or more assessment engines to perform actions, including;
  collecting performance content that includes information associated with one or more performances of one or more activities;
 employing one or more classifiers to perform actions, including:
  classifying the performance content to determine one or more occurrences of one or more features of the performance content; and
  classifying assessment content to determine one or more scores that are associated with one or more features included in the one or more performances, wherein the assessment content includes information associated with one or more features of the one or more performances of the one or more activities; and providing one or more correlation values associated with the one or more performances based on historical performance content, assessment content, and scores;

employing the one or more correlation values to provide feedback to a subject that performed at least a portion of the one or more activities, wherein the feedback includes one or more of a recommendation to improve real time performances of the one or more activities, training materials to improve future performances of the one or more activities, a capability of the subject for efficiency and effectiveness, or a rank for scheduling the subject to perform the one or more activities in the future; and providing a report that includes a localized evaluation of the one or more performances based on the correlation values, performance content, assessment content, feedback, and scores.

2. The method of claim 1, wherein-collecting the performance content includes:

receiving a video stream of an activity performed by one or more subjects; and generating the assessment content based on the one or more performances included in the video stream.

3. The method of claim 1, wherein classifying the assessment content further comprises:

classifying unstructured content that is provided by different sources; and further determining the one or more scores based on the classification of the unstructured content.

4. The method of claim 1, wherein employing one or more assessment engines to perform actions, further comprises:

providing real-time feedback to one or more subjects that are performing the one or more activities; and collecting one or more responses from the one or more subjects that are associated with the real-time feedback.

5. The method of claim 1, further comprising updating the one or more classifiers based on the one or more correlation values.

6. The method of claim 1, wherein employing one or more assessment engines to perform actions, further comprises:

extracting a portion of the performance content associated with the assessment content based on the one or more scores that exceed a defined value; and providing the extracted portion of the performance content and its assessment content to a classification processing engine for use as training data.

7. The method of claim 1, wherein providing one or more correlation values associated with the one or more performances, further comprises:

receiving a timeline that defines one or more steps that comprise the one or more activities;

correlating the one or more performances with the timeline based on occurrence of the one or more steps; and modifying the one or more classifiers based on the correlation of the one or more performances with the timeline.

8. A system for assessing performances of physical activities, comprising:

a network computer, comprising:
a transceiver that communicates over the network;
a memory that stores at least instructions; and
one or more processor devices that execute instructions that perform actions, including:
employing one or more assessment engines to perform actions, including:
collecting performance content that includes information associated with one or more performances of one or more activities;
employing one or more classifiers to perform actions, including:
classifying the performance content to determine one or more occurrences of one or more features of the performance content; and
classifying assessment content to determine one or more scores that are associated with one or more features included in the one or more performances, wherein the assessment content includes information associated with one or more features of the one or more performances of the one or more activities; and
providing one or more correlation values associated with the one or more performances based on historical performance content, assessment content, and scores; and
employing the one or more correlation values to provide feedback to a subject that performed at least a portion of the one or more activities, wherein the feedback includes one or more of a recommendation to improve real time performances of the one or more activities, training materials to improve future performances of the one or more activities, a capability of the subject for efficiency and effectiveness, or a rank for scheduling the subject to perform the one or more activities in the future; and
providing a report that includes a localized evaluation of the one or more performances based on the correlation values, performance content, assessment content, feedback, and scores; and
a client computer, comprising:
a transceiver that communicates over the network;
a memory that stores at least instructions; and
one or more processor devices that execute instructions that perform actions, including:
providing one or more of the performance content or the assessment content.

9. The system of claim 8, wherein collecting the performance content includes:

receiving a video stream of an activity performed by one or more subjects; and generating the assessment content based on the one or more performances included in the video stream.

10. The system of claim 8, wherein classifying the assessment content further comprises:

classifying unstructured content that is provided by different sources; and further determining the one or more scores based on the classification of the unstructured content.

11. The system of claim 8, wherein employing one or more assessment engines to perform actions, further comprises:

providing real-time feedback to one or more subjects that are performing the one or more activities; and collecting one or more responses from the one or more subjects that are associated with the real-time feedback.

12. The system of claim 8, further comprising updating the one or more classifiers based on the one or more correlation values.

13. The system of claim 8, wherein employing one or more assessment engines to perform actions, further comprises:
  extracting a portion of the performance content associated with the assessment content based on the one or more scores that exceed a defined value; and
  providing the extracted portion of the performance content and its assessment content to a classification processing engine for use as training data.

14. The system of claim 8, wherein providing one or more correlation values associated with the one or more performances, further comprises:
  receiving a timeline that defines one or more steps that comprise the one or more activities;
  correlating the one or more performances with the timeline based on occurrence of the one or more steps; and
  modifying the one or more classifiers based on the correlation of the one or more performances with the timeline.

15. A processor readable non-transitory storage media that includes instructions for assessing performances of physical activities, wherein execution of the instructions by one or more hardware processors performs actions, comprising:
  employing one or more assessment engines to perform actions, including:
    collecting performance content that includes information associated with one or more performances of one or more activities;
    employing one or more classifiers to perform actions, including:
      classifying the performance content to determine one or more occurrences of one or more features of the performance content; and
      classifying assessment content to determine one or more scores that are associated with one or more features included in the one or more performances, wherein the assessment content includes information associated with one or more features of the one or more performances of the one or more activities; and
    providing one or more correlation values associated with the one or more performances based on historical performance content, assessment content, and scores; and
    employing the one or more correlation values to provide feedback to a subject that performed at least a portion of the one or more activities, wherein the feedback includes one or more of a recommendation to improve real time performances of the one or more activities, training materials to improve future performances of the one or more activities, a capability of the subject for efficiency and effectiveness, or a rank for scheduling the subject to perform the one or more activities in the future; and
    providing a report that includes a localized evaluation of the one or more performances based on the correlation values, performance content, assessment content, feedback, and scores.

16. The media of claim 15, wherein collecting the performance content includes:
  receiving a video stream of an activity performed by one or more subjects; and
  generating the assessment content based on the one or more performances included in the video stream.

17. The media of claim 15, wherein classifying the assessment content further comprises:
  classifying unstructured content that is provided by different sources; and
  further determining the one or more scores based on the classification of the unstructured content.

18. The media of claim 15, wherein employing one or more assessment engines to perform actions, further comprises:
  providing real-time feedback to one or more subjects that are performing the one or more activities; and
  collecting one or more responses from the one or more subjects that are associated with the real-time feedback.

19. The media of claim 15, further comprising updating the one or more classifiers based on the one or more correlation values.

20. The media of claim 15, wherein employing one or more assessment engines to perform actions, further comprises:
  extracting a portion of the performance content associated with the assessment content based on the one or more scores that exceed a defined value; and
  providing the extracted portion of the performance content and its assessment content to a classification processing engine for use as training data.

21. The media of claim 15, wherein providing one or more correlation values associated with the one or more performances, further comprises:
  receiving a timeline that defines one or more steps that comprise the one or more activities;
  correlating the one or more performances with the timeline based on occurrence of the one or more steps; and
  modifying the one or more classifiers based on the correlation of the one or more performances with the timeline.

22. A network computer for assessing performances of physical activities, comprising:
  a transceiver that communicates over the network;
  a memory that stores at least instructions; and
  one or more processor devices that execute instructions that perform actions, including:
    employing one or more assessment engines to perform actions, including:
  collecting performance content that includes information associated with one or more performances of one or more activities;
  employing one or more classifiers to perform actions, including:
    classifying the performance content to determine one or more occurrences of one or more features of the performance content; and
    classifying assessment content to determine one or more scores that are associated with one or more features included in the one or more performances, wherein the assessment content includes information associated with one or more features of the one or more performances of the one or more activities; and
  providing one or more correlation values associated with the one or more performances based on historical performance content, assessment content, and scores; and
  employing the one or more correlation values to provide feedback to a subject that performed at least a portion of the one or more activities, wherein the feedback includes one or more of a recommendation to improve real time performances of the one or more activities, training materials to improve future performances of the one or more activities, a capability of the subject for efficiency and effectiveness, or a rank for scheduling the subject to perform the one or more activities in the future; and providing a report that includes a localized evaluation of the one or more performances based on the correlation values, performance content, assessment content, feedback, and scores.

23. The network computer of claim 22, wherein collecting the performance content includes:

receiving a video stream of an activity performed by one or more subjects; and generating the assessment content based on the one or more performances included in the video stream.

24. The network computer of claim 22, wherein classifying the assessment content further comprises:

classifying unstructured content that is provided by different sources; and further determining the one or more scores based on the classification of the unstructured content.

25. The network computer of claim 22, wherein employing one or more assessment engines to perform actions, further comprises:

providing real-time feedback to one or more subjects that are performing the one or more activities; and collecting one or more responses from the one or more subjects that are associated with the real-time feedback.

26. The network computer of claim 22, further comprising updating the one or more classifiers based on the one or more correlation values.

27. The network computer of claim 22, wherein employing one or more assessment engines to perform actions, further comprises:

extracting a portion of the performance content associated with the assessment content based on the one or more scores that exceed a defined value; and providing the extracted portion of the performance content and its assessment content to a classification processing engine for use as training data.

28. The network computer of claim 22, wherein providing one or more correlation values associated with the one or more performances, further comprises:

receiving a timeline that defines one or more steps that comprise the one or more activities;

correlating the one or more performances with the timeline based on occurrence of the one or more steps; and modifying the one or more classifiers based on the correlation of the one or more performances with the timeline.

* * * * *

UNITED STATES PATENT AND TRADEMARK OFFICE
CERTIFICATE OF CORRECTION

PATENT NO. : 10,147,052 B1  
APPLICATION NO. : 15/882938  
DATED : December 4, 2018  
INVENTOR(S) : Lendvay et al.

Page 1 of 2

It is certified that error appears in the above-identified patent and that said Letters Patent is hereby corrected as shown below:

In the Drawings

In Fig. 2, Sheet 2 of 16, delete "CLIENT COMPTER" and insert -- CLIENT COMPUTER --, therefor.

In Fig. 7, Sheet 7 of 16, delete " 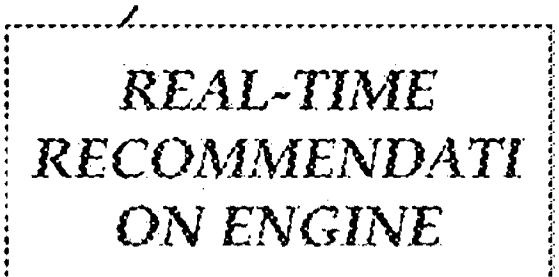 " and insert -- 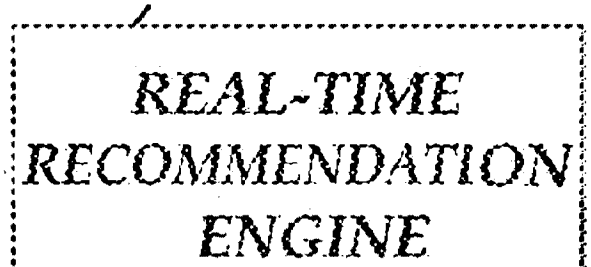 --, therefor.

In Fig. 14, Sheet 14 of 16, for Tag "1406", Line 3, delete "exam" and insert -- exam) --, therefor.

In the Specification

In Column 7, Line 7, delete "documenting computers 102-107" and insert -- documenting computers 112-118 --, therefor.

Signed and Sealed this  
Thirtieth Day of July, 2019

Andrei Iancu  
*Director of the United States Patent and Trademark Office*

CERTIFICATE OF CORRECTION (continued)
U.S. Pat. No. 10,147,052 B1

In Column 7, Lines 35-36, delete "documenting computers 102-107" and insert -- documenting computers 112-118 --, therefor.

In Column 12, Line 63, delete "Mobile computer's 200" and insert -- client computer's 200 --, therefor.

In Column 14, Line 39, delete "GPS 338," and insert -- GPS 358, --, therefor.

In Column 15, Lines 4-5, delete "as a various" and insert -- as various --, therefor.

In Column 17, Line 33, delete "clarity FIG. 4" and insert -- clarity, FIG. 4 --, therefor.

In Column 19, Line 54, delete "than are" and insert -- that are --, therefor.

In Column 19, Line 56, delete "may be include" and insert -- may include --, therefor.

In Column 20, Line 2, delete "may uploaded" and insert -- may be uploaded --, therefor.

In Column 30, Line 4, delete "user-interface 1400" and insert -- user-interface 1500 --, therefor.

In the Claims

In Column 30, Line 56, in Claim 1, delete "including;" and insert -- including: --, therefor.

In Column 31, Line 24, in Claim 2, delete "wherein-collecting" and insert -- wherein collecting --, therefor.